(12) United States Patent
Hampden-Smith et al.

(10) Patent No.: US 7,968,191 B2
(45) Date of Patent: Jun. 28, 2011

(54) MODIFIED CARBON PRODUCTS AND THEIR APPLICATIONS

(75) Inventors: Mark J. Hampden-Smith, Albuquerque, NM (US); James Caruso, Albuquerque, NM (US); Paolina Atanassova, Albuquerque, NM (US); Agathagelos Kyrlidis, Cambridge, MA (US)

(73) Assignee: Cabot Corporation, Boston, MA (US)

( * ) Notice: Subject to any disclaimer, the term of this patent is extended or adjusted under 35 U.S.C. 154(b) by 2 days.

(21) Appl. No.: 11/081,771

(22) Filed: Mar. 15, 2005

(65) Prior Publication Data

US 2005/0244644 A1 Nov. 3, 2005

Related U.S. Application Data

(60) Provisional application No. 60/553,612, filed on Mar. 15, 2004, provisional application No. 60/553,413, filed on Mar. 15, 2004, provisional application No. 60/553,672, filed on Mar. 15, 2004, provisional application No. 60/553,611, filed on Mar. 15, 2004, provisional application No. 60/555,888, filed on Mar. 24, 2004.

(51) Int. Cl.
*B32B 9/00* (2006.01)
(52) U.S. Cl. .................................................... 428/408
(58) Field of Classification Search .................. 428/408; 423/445, 445 R; 977/742
See application file for complete search history.

(56) References Cited

U.S. PATENT DOCUMENTS

| | | | |
|---|---|---|---|
| 4,601,887 A | 7/1986 | Dorn et al. | |
| 5,807,494 A | 9/1998 | Boes et al. | |
| 5,851,280 A * | 12/1998 | Belmont et al. | 106/472 |
| 5,900,029 A | 5/1999 | Belmont | |
| 6,103,380 A | 8/2000 | Devonport | |
| 6,280,871 B1 | 8/2001 | Tosco et al. | |
| 6,328,894 B1 | 12/2001 | Chan et al. | |
| 6,337,358 B1 | 1/2002 | Whitehouse et al. | |
| 6,338,809 B1 | 1/2002 | Hampden-Smith et al. | |
| 6,350,519 B1 | 2/2002 | Devonport | |
| 6,368,239 B1 | 4/2002 | Devonport et al. | |
| 6,372,820 B1 | 4/2002 | Devonport | |
| 6,534,569 B2 | 3/2003 | Mahmud et al. | |
| 6,551,393 B2 | 4/2003 | Devonport et al. | |
| 6,630,268 B2 | 10/2003 | Tosco et al. | |
| 6,660,680 B1 | 12/2003 | Hampden-Smith et al. | |
| 6,664,312 B2 | 12/2003 | Devonport | |
| 6,852,158 B2 | 2/2005 | Belmont et al. | |
| 6,875,274 B2 * | 4/2005 | Wong et al. | 117/105 |
| 6,881,511 B1 | 4/2005 | Tosco et al. | |
| 6,967,183 B2 * | 11/2005 | Hampden-Smith et al. | 502/101 |
| 7,024,029 B2 | 4/2006 | Akahori | |
| 7,255,954 B2 * | 8/2007 | Hampden-Smith et al. | 429/40 |
| 2002/0004028 A1 | 1/2002 | Margrave | |

(Continued)

FOREIGN PATENT DOCUMENTS

RU 2154077 C2 8/2000

(Continued)

OTHER PUBLICATIONS

PCT/US2005/008666 Aug. 4, 2006 International Search Report.

(Continued)

*Primary Examiner* — Angela Ortiz
*Assistant Examiner* — Daniel Miller

(57) ABSTRACT

Modified carbon products including a metal group attached to the modified carbon product. The modified carbon products are particularly useful for various applications such as catalysis, electronic conduction, ionic conduction, absorbents, heat transfer and luminescence.

30 Claims, 9 Drawing Sheets

U.S. PATENT DOCUMENTS

| | | |
|---|---|---|
| 2002/0122578 A1 | 9/2002 | Akahori |
| 2003/0017379 A1 | 1/2003 | Menashi |
| 2003/0022055 A1 | 1/2003 | Menashi |
| 2005/0221141 A1 | 10/2005 | Hampden-Smith et al. |
| 2005/0233158 A1* | 10/2005 | Tour et al. .................... 428/457 |
| 2005/0233203 A1 | 10/2005 | Hampden-Smith et al. |
| 2008/0317659 A1 | 12/2008 | Dolmatov |

FOREIGN PATENT DOCUMENTS

| | | |
|---|---|---|
| SU | 1061699 A | 10/1979 |
| WO | WO 96/18059 A1 | 6/1996 |
| WO | WO 97/32571 A1 | 9/1997 |
| WO | WO 03/099946 | 12/2003 |

OTHER PUBLICATIONS

PCT/US2005/008666 Nov. 23, 2006 International Preliminary Report on Patentability.

English translation of Office Action from corresponding Russian Federation Patent Application No. 2006136378, dated Oct. 12, 2009 (5 pages).

English translation of Office Action from corresponding Russian Federation Patent Application No. 2006136378, dated Apr. 1, 2009 (5 pages).

* cited by examiner

MODIFIED CARBON PRODUCTS AND THEIR APPLICATIONS

CROSS-REFERENCE TO RELATED APPLICATIONS

Pursuant to 35 U.S.C. §119(e), this patent application claims a priority benefit to: (a) U.S. Provisional Patent Application No. 60/553,612 entitled "Modified Carbon Products and Their Use in Gas Diffusion Layers" filed Mar. 15, 2004; (b) U.S. Provisional Patent Application No. 60/553,413 entitled "Modified Carbon Products and Their Use in Electrocatalysts and Electrode Layers" filed Mar. 15, 2004; (c) U.S. Provisional Patent Application No. 60/553,672 entitled "Modified Carbon Products and Their Use in Proton Exchange Membranes" filed Mar. 15, 2004; (d) U.S. Provisional Patent Application No. 60/553,611 entitled "Modified Carbon Products and Their Use in Bipolar Plates" filed Mar. 15, 2004; and (e) U.S. Provisional Patent Application No. 60/555,888 entitled "Modified Carbon Products and Their Applications" filed Mar. 24, 2004. Each of the above referenced provisional patent applications is incorporated herein by reference in its entirety.

BACKGROUND OF THE INVENTION

1. Field of the Invention

The present invention relates to the use of modified carbon products in a number of applications. More particularly, the present invention relates to the use of modified carbon products and metal-functionalized modified carbon products in applications such as catalysis, electronic and ionic conduction, adsorption, heat transfer and luminescence.

2. Description of Related Art

Carbon is used in a wide variety of industrial applications that take advantage of its intrinsic characteristics. These characteristics include good electrical conductivity, high surface area, black color, abrasion resistance and intercalation. The electrical conductivity can be controlled, with graphitic materials being more conductive compared to amorphous carbon. This leads to numerous applications in the battery industry and fuel cell industry where carbon is used as an electrode material. The typically high surface area with somewhat controllable porosity results in the use of carbon in applications such as catalyst and electrocatalyst supports, where the high surface area produces highly dispersed supported catalysts and absorbents. In the case of electrocatalysts, the characteristics of high surface area and electrical conductivity are combined to create conductive catalyzed gas diffusion electrodes.

Carbon is also intensely black and a relatively small amount of carbon can be used to impart an intensely black color to objects. As a result, it is used to fill polymers to make black plastics as well as being used in printing inks to create text and images such as newspaper print or small office/home office printed products. As an extension of this attribute, the inclusion of a filler results in strengthening of the polymer or plastic leading to improved mechanical strength and abrasion resistance and has resulted in the extensive use of carbon in vehicle tires, for example.

In addition, the layer structure of the graphite polymorph of carbon can be intercalated with various materials. An example is lithium in lithium ion batteries.

The surface of the carbon material does not play an active role in most of the foregoing applications. Where it does play a role (e.g., electrocatalysis in zinc-air batteries), it is a very specific role limited to the particular composition of the carbon surface. Indeed, in many applications of carbon materials, the surface of the carbon is coated with surfactants to enhance the dispersion characteristics of the carbon in another medium such as an aqueous, non-aqueous or polymeric vehicle. However, in many applications, the surface chemistry dominates the function of the material in an application, in many cases independent of the characteristics of the bulk material. For example, applications that require reversible specific binding of ions or molecules to surfaces for applications such as sensors, adsorbents, catalysis, power sources, displays, electrodialysis, ionic transport and separations are often independent of the composition of the bulk material. Therefore it would be extremely valuable to have a versatile method to create a wide variety of functionalization on a surface. It would be even more valuable if the surface on which the functionalization is developed is part of a bulk material that has characteristics that further enhance the functionalization of the surface.

A method for the functionalization of carbon products has been described in U.S. Pat. No. 5,900,029 by Belmont et al., which is incorporated herein by reference in its entirety. The process described therein is referred to herein as the Belmont process. It was shown by Belmont et al. that a wide variety of organic functional groups can be chemically bonded to the surface of almost any form of carbon using diazonium salt chemistry. To date, applications of these "surface modified carbons" or "modified carbon products" have focused on improving the dispersion characteristics of the carbon products in other media such as inks, pastes and polymers.

Belmont et al. discloses a modified carbon black product and a method for making a modified carbon black product. The modified carbon black is formed by reacting at least one diazonium salt with carbon black in the absence of an externally applied electric current sufficient to reduce the diazonium salt. It is disclosed that the modified carbon black products can be utilized in plastic compositions, rubber compositions, paper compositions and textile compositions.

SUMMARY OF THE INVENTION

According to one embodiment of the present invention, the metal functionalization of surface modified carbon is provided where the functional organic groups are used to bind metal species that lead to a wide variety of functionality based on the presence of the metal species bound to the surface of the carbon products. In one embodiment, the metal is bonded to bulk carbon material for applications such as electrodialysis, electrocatalysis and electrical swing adsorption. In other embodiments, the carbon is only present at the surface of or otherwise combined with another phase such that the bulk properties of the material are less influenced by the presence of the carbon.

According to one embodiment of the present invention, a modified carbon product is provided. The modified carbon product includes a functional group covalently attached to a carbon surface and a metal group attached to the functional group.

The metal group can be attached to the functional group either ionically or covalently. FIG. 1 illustrates various applications for the modified carbon products according to the present invention for coordinated metal species and for ion-exchangeable metal species. According to one aspect, the modified carbon product is used in electrodialysis. According to another aspect, the modified carbon product is used in an electrical conductor. According to another aspect, the modified carbon product is used in an ionic conductor. According to yet another aspect, the modified carbon product is used for immunoassays. According to another aspect, the modified carbon product is used for luminescence, such as electroluminescence.

According to another aspect, the modified carbon product is used in a thermally conductive fluid. According to another aspect, the modified carbon product is used for hydrogen storage. According to another aspect, the modified carbon product is used for catalysis. According to still another aspect, the modified carbon product is used for capacitors. According to still another aspect, the modified carbon product is used for sensors.

According to another embodiment of the present invention, a method for the manufacture of a modified carbon product is provided. The method can include the steps of providing a carbon support, modifying the carbon support with a functional group, and attaching a metallic species to the functional group.

According to one aspect, the carbon support comprises carbon black. According to another aspect, the functional group is ionically charged and coordinating. According to another aspect, the metallic species is covalently attached to the functional group.

According to another embodiment, a modified carbon product comprising a functional group covalently attached to a carbon surface is provided, where the modified carbon product is used for hydrogen storage.

According to another embodiment, a modified carbon product comprising a functional group covalently attached to a carbon surface is provided, where the modified carbon product is used for catalysis.

According to another embodiment, a modified carbon product comprising a functional group covalently attached to a carbon surface is provided, where the modified carbon product is used for capacitors.

According to still another embodiment, a modified carbon product comprising a functional group covalently attached to a carbon surface is provided, where the modified carbon product is used for a thermally conductive fluid.

According to yet another embodiment, a modified carbon product comprising a functional group covalently attached to a carbon surface is provided, where the modified carbon product is used for luminescence.

According to another embodiment, a modified carbon product comprising a functional group covalently attached to a carbon surface is provided, where the modified carbon product is used for electro dialysis.

These and other embodiments and aspects of the present invention will become apparent from the following description of the invention.

DETAILED DESCRIPTION OF THE INVENTION

Figure 1:
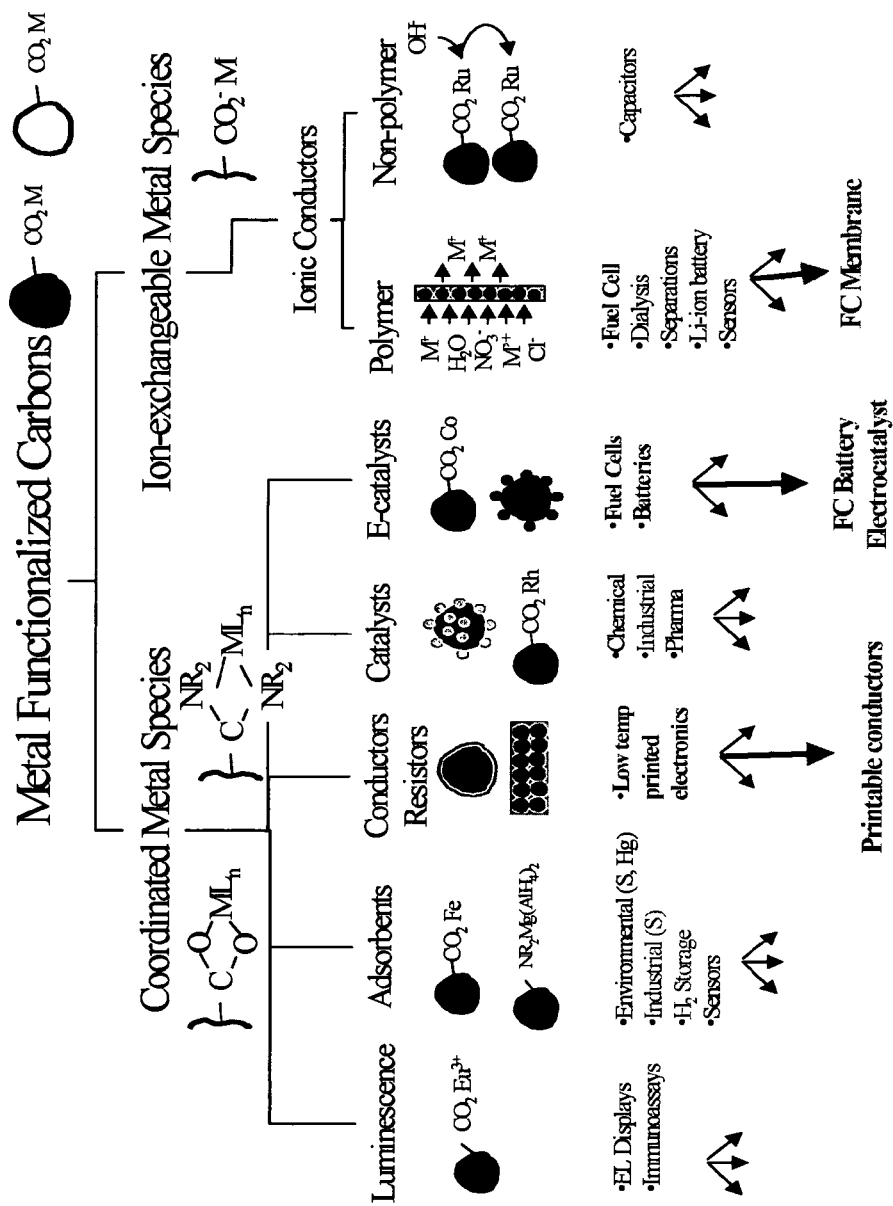
FIG. 1 illustrates various applications for modified carbon products and metal-functionalized modified carbon products according to the present invention.

The present invention relates to the use of modified carbon products in applications ranging from ion conduction membranes to electronics, as illustrated in FIG. 1. As used herein, a modified carbon product refers to a carbon material having an organic group attached to the carbon. A method for the production of such modified carbon products is described in U.S. Pat. No. 5,900,029 by Belmont et al., which is incorporated herein by reference in its entirety. The process for fabricating the modified carbon product includes the step of reacting at least one diazonium salt with a carbon material, preferably in the absence of an externally applied electric current sufficient to reduce the diazonium salt. Another process includes the step of reacting at least one diazonium salt with a carbon product in a protic reaction medium. The diazonium salt can include the organic group to be attached to the carbon. For example, the organic group can be an aliphatic group, a cyclic organic group or an organic compound having an aliphatic portion and a cyclic portion. The organic group can be substituted or unsubstituted and can be branched or unbranched.

The carbon material can be in the form of, for example, particulate carbon such as carbon black, activated carbon, bulk carbon, carbon flake, carbon fiber, carbon nanotubes and the like including carbon coated materials, carbon composites or carbon containing-materials including carbon films or materials containing carbon films. Also useful are carbon cloths and carbon paper. The crystalline nature of the carbon can range from vitreous carbon to graphite carbon.

According to one embodiment of the present invention, the modified carbon product is modified carbon black. Carbon black is homologous to graphite and consists of multiple layers of sheet carbon separated by several angstroms. The primary particles have a size in the range of from about 9 nanometers to 150 nanometers and the surface area is typically from about 20 m²/g to 1500 m²/g. In addition, the carbon material may also comprise a composite carbon material wherein carbon-based material comprises only a portion of the material by weight or volume. Examples of these composite materials include materials comprised of metal oxides, sulfides, carbides, nitrides and the like, in which the carbon based material may be distributed on all or part of the surface or may be incorporated as particles such that the surface of the second phase remains unaffected.

The native (unmodified) carbon surface is relatively inert to most organic reactions and the attachment of specific organic groups at high coverage levels has traditionally been difficult. The Belmont et al. process significantly improved the ability to modify carbon surfaces with such organic groups. The organic groups are covalently bonded to the carbon surface and the groups are highly stable and do not desorb.

Generally, the carbon is modified via a functionalizing agent of the form:

where: X reacts with the carbon surface;
R is a linking group; and
Y is a functional group.

Figure 2:
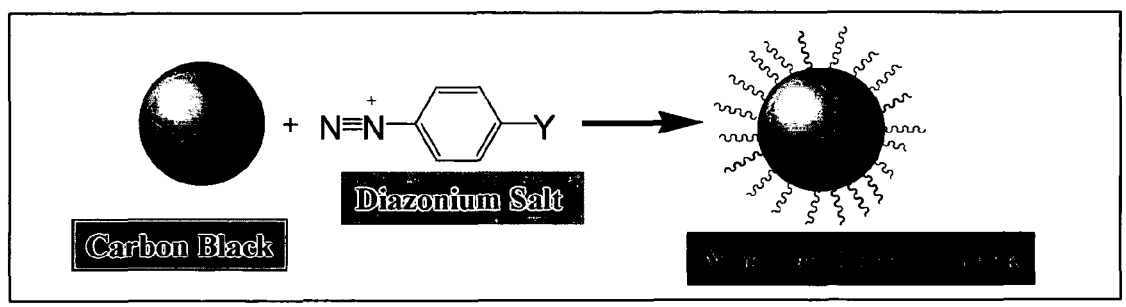
FIG. 2 illustrates the chemical surface funtionalization of carbon black by the Belmont process.

FIG. 2 illustrates the surface modification of a carbon particle according to the Belmont process.

Accordingly, the carbon can be modified to alter the surface energy, dispersibility, aggregate size and size distribution, dispersion, viscosity and chemical reactivity of the carbon. Examples of functional organic groups that can be used to modify the carbon black surface according to the present invention include those that are proton conducting such as sulfonic and phosphonic acids or charged (electrostatic) groups, such as sulfonate, carboxylate and tertiary amine salts. In addition, polymer (steric) groups such as acrylic, polystyrene, polyethylene oxide (PEO), polypropylene oxide (PPO) and polyethylene glycol (PEG) can be used as the functional group as well as neutral groups such as amines, aliphatics and cyclics. Particularly preferred according to one embodiment of the present invention are functional groups that alter the hydrophobic or hydrophilic nature of the carbon surface, or that can chemically bind metal ions or metal compounds or that impart proton conductivity. Examples of such functional groups are listed in Table I.

TABLE I

| Types of Functional Groups (Y) | Examples (RY) |
|---|---|
| Proton conductivity | $(C_6H_4)CO_2H$ or $(C_{10}H_6)PO_3NaH$ |
| Hydrophobic, Hydrophilic | $(C_6H_4)CF_3$, $(C_6H_4)SO_3H$ |
| Metal coordinating | $(C_{10}H_6)CO_2H$ or $(C_6H_4)NH_2$ |

Figure 3:
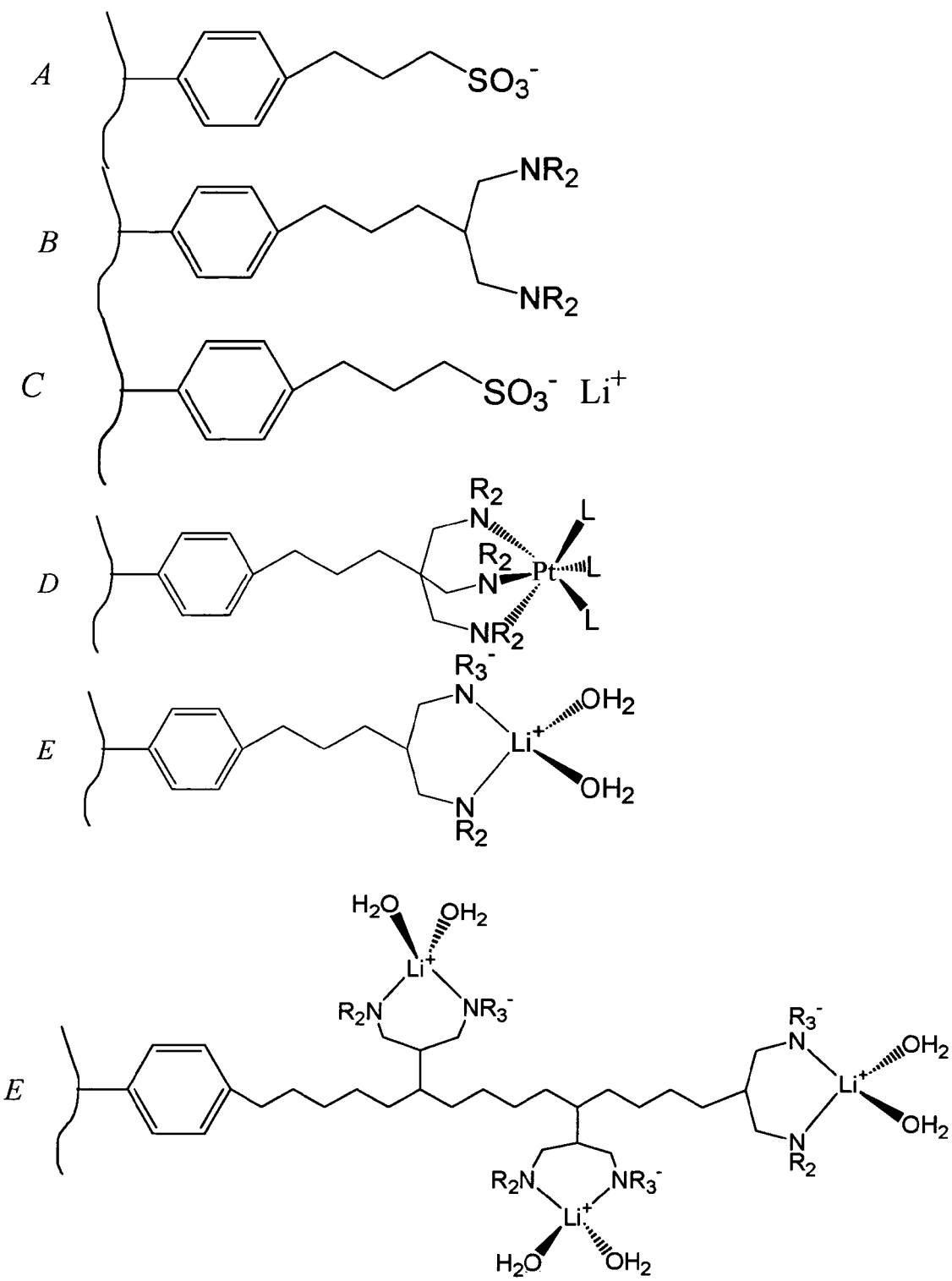
FIG. 3 illustrates different metal-chelating surface functional groups according to the present invention.

Other examples of specific organic groups are listed in U.S. Pat. No. 5,900,029 by Belmont et al. and some are illustrated in FIG. 3.

Other preferred functional groups include electron donors or electron acceptors. Particularly preferred groups for the metal functionalized groups according to the present invention include those that are both ionically charged and are coordinating, such as $-SO_3H(-SO_3^-)$, $-NR_3^+$ (where R=an alkyl or aryl group or hydrogen or any combination thereof), $-NR_2$ (where R=an alkyl or aryl group or hydrogen or any combination thereof), $-PR_2$ (where R=an alkyl or aryl group or hydrogen or any combination thereof), $-CO_2H(-CO_2^-)$, $-CONR_2$ and $-PO_3H_2$. In addition, chelating ligands with multiple functionality are preferred in order to bind metal species more strongly. Examples of preferred chelating ligands include polyamines, polyphosphines, polycarboxylates and ligands with mixed functionality such as aminoacids, EDTA and prochiral ligands to create optically active metal complexes (see FIG. 3).

The present invention relates to the use of modified carbon products in a variety of applications that include catalysis, electronics, ion conduction, adsorbents, heat transfer and luminescence applications. The majority of these applications utilize modified carbon products that offer the ability to metal functionalize, i.e., the ability to coordinate or bind metals, metal ions or metal-containing species, which are collectively referred to herein as metal groups. In the context of the present invention, metal functionalization refers to any of the following situations:
  i) the binding of a covalent metal-containing molecule to the surface of the modified carbon product;
  ii) the binding of an ionic metal-containing species to the surface of the modified carbon product; or
  iii) the presence of a metal-containing species on the surface or derived from the surface of the modified carbon product where the metal species may be a pure metal, a metal oxide, metal halide, metal sulfide, metal boride, metal nitride, metal carbide or other inorganic metal-containing compound.

The modified carbon products according to the present invention can be manufactured in accordance with the Belmont process.

According to one embodiment of the present invention, modified carbon products that are useful in accordance with the present invention can be manufactured using spray processing, spray conversion or spray pyrolysis, the methods being collectively referred to herein as spray processing.

Spray processing generally includes the steps of: providing a liquid precursor suspension which includes the carbon and the diazonium salt or a precursor to the diazonium salt; atomizing the precursor to form dispersed liquid precursor droplets; and removing liquid from the dispersed liquid precursor droplets to form the modified carbon black particles.

Preferably, the spray processing method combines: (i) the drying of the diazonium salt, carbon containing droplets; and (ii) the conversion of the diazonium salt to a linking group and functional group covalently bound to a carbon surface, in one step such that both the removal of the solvent and the conversion of a precursor occur essentially simultaneously. In another embodiment, the spray processing method achieves the drying of the droplets and the conversion to a linking group and functional group can occur in a second step. Combined with a short reaction time, this enables control over the properties of the linking group and functional group bound to the carbon product. By varying reaction time, temperature, type of carbon product and type of precursors, the spray method can produce morphologies and structures that yield improved performance.

Preferably, with the spray processing method, the modified carbon particles are formed while the diazonium salt phase is in intimate contact with the surface of the carbon particles and the diazonium salt is rapidly reacted on the surface of the carbon particles. The reaction of the diazonium salt preferably occurs over a very short period of time. Preferably, the diazonium salt is exposed to the elevated reaction temperature to form the modified carbon product for not more than about 600 seconds, more preferably not more than about 100 seconds and even more preferably not more than about 10 seconds.

Preferably, the spray processing method is capable of simultaneously forming a spherical aggregate modified carbon particle structure. The spherical aggregate particles form as a result of the formation and drying of the droplets during spray processing and the properties of the structure are influenced by the characteristics of the carbon particles such as the particle size, particle size distribution and surface area.

Spray processing methods for modified carbon production can be grouped by reference to several different attributes of the apparatus used to carry out the method. These attributes include: the main gas flow direction (vertical or horizontal); the type of atomizer (submerged ultrasonic, ultrasonic nozzle, two-fluid nozzle, single nozzle pressurized fluid); the type of gas flow (e.g., laminar with no mixing, turbulent with no mixing, co-current of droplets and hot gas, countercurrent of droplets and gas or mixed flow); the type of heating (e.g., hot wall system, hot gas introduction, combined hot gas and hot wall, plasma or flame); and the type of powder collection system (e.g., cyclone, bag house, electrostatic or settling).

For example, modified carbon particles can be prepared by starting with an aqueous-based precursor liquid consisting of colloidal carbon and a diazonium salt. The processing temperature of the precursor droplets can be controlled so the diazonium salt reacts, leaving the carbon intact but surface functionalized. The precursor liquid can also include a protic reaction medium.

The first step in the process can include the evaporation of the solvent (typically water) as the droplet is heated resulting in a particle of dried solids and salts. A number of methods to deliver heat to the particle are possible: horizontal hot-wall tubular reactors, spray drier and vertical tubular reactors can be used, as well as plasma, flame and laser reactors. As the particles experience either higher temperature or longer time at a specific temperature, the diazonium salt reacts. Preferably with the spray processing method, the temperature and time that the droplets/particles experience can be controlled and therefore the properties of the resulting linking group and functional group on the carbon surface can also be controlled.

The atomization technique for generating the droplets has a significant influence over the characteristics of the final modified carbon particles such as the spread of the aggregate particle size distribution (PSD), as well as the production rate of the powder. In extreme cases, some techniques cannot atomize fluids with even moderate carbon particle loadings or high viscosities. Several methods exist for the atomization of precursor compositions containing suspended particulates such as carbon. These methods include but are not limited to: ultrasonic transducers (usually at a frequency of 1-3 MHz); ultrasonic nozzles (usually at a frequency of 10-150 KHz); rotary atomizers; two-fluid nozzles; and pressure atomizers.

Ultrasonic transducers are generally submerged in a liquid and the ultrasonic energy produces atomized droplets on the surface of the liquid. Two basic ultrasonic transducer disc configurations—planar and point source—can be used. Deeper fluid levels can be atomized using a point source configuration since the energy is focused at a point that is some distance above the surface of the transducer. The scale-up of submerged ultrasonic transducers can be accomplished by placing a large number of ultrasonic transducers in an array. Such a system is illustrated in U.S. Pat. No. 6,103,393 by Kodas et al. and U.S. Pat. No. 6,338,809 by Hampden-Smith et al., the disclosure of each of which is incorporated herein by reference in its entirety.

Scale-up of nozzle systems can be accomplished by either selecting a nozzle with a larger capacity or by increasing the number of nozzles used in parallel. Typically, the droplets produced by nozzles are larger than those produced by ultrasonic transducers. Particle size is also dependent on the gas flow rate. For a fixed liquid flow rate, an increased airflow decreases the average droplet size and a decreased airflow increases the average droplet size. It is difficult to change droplet size without varying the liquid or airflow rates. However, two-fluid nozzles have the ability to process larger volumes of liquid per time than ultrasonic transducers.

Ultrasonic spray nozzles also use high frequency energy to atomize a fluid. Ultrasonic spray nozzles have some advantages over single or two-fluid nozzles such as the low velocity of the spray leaving the nozzle and lack of associated gas flow. The nozzles are available with various orifice sizes and orifice diameters that allow the system to be scaled for the desired production capacity. In general, higher frequency nozzles are physically smaller, produce smaller droplets, and have a lower flow capacity than nozzles that operate at lower frequencies. A drawback of ultrasonic nozzle systems is that scaling up the process by increasing the nozzle size increases the average particle size. If a particular particle size is required, then the maximum production rate per nozzle is set. If the desired production rate exceeds the maximum production rate of the nozzle, additional nozzles or complete production units will be required to achieve the desired production rate.

The shape of the atomizing surface determines the shape and spread of the spray pattern. Conical, microspray and flat atomizing surface shapes are available. The conical atomizing surface provides the greatest atomizing capability and has a large spray envelope. The flat atomizing surface provides almost as much flow as the conical, but limits the overall diameter of the spray. The microspray atomizing surface is for very low flow rates where narrow spray patterns are needed. These nozzles are preferred for configurations where minimal gas flow is required in association with the droplets.

Particulate carbon suspensions may present several problems with respect to atomization. For example, submerged ultrasonic atomizers re-circulate the suspension through the generation chamber and the suspension concentrates over time. Further, some fraction of the liquid atomizes without carrying the suspended carbon particulates. Other problems encountered when using submerged ultrasonic transducers is that the transducer discs can become coated with the particles over time. Further, the generation rate of carbon suspensions is very low using submerged ultrasonic transducer discs. This is due in part to energy being absorbed or reflected by the suspended particles.

For spray drying, the aerosol can be generated using three basic methods. These methods differ in the type of energy used to break the liquid masses into small droplets. Rotary atomizers (utilization of centrifugal energy) make use of spinning liquid droplets off of a rotating wheel or disc. Rotary atomizers are useful for co-current production of droplets in the range of 20 to 150 μm in diameter. Pressure nozzles (utilization of pressure energy) generate droplets by passing a fluid under high pressure through an orifice. These can be used for both co-current and mixed-flow reactor configurations and typically produce droplets in the range of 50 to 300 μm. Multiple fluid nozzles such as a two fluid nozzle (utilization of kinetic energy) produce droplets by passing a relatively slow moving fluid through an orifice while shearing the fluid stream with a relatively fast moving gas stream. As with pressure nozzles, multiple fluid nozzles can be used with both co-current and mixed-flow spray dryer configurations. This type of nozzle can typically produce droplets in the range of 5 to 200 μm.

For example, two-fluid nozzles are used to produce aerosol sprays in many commercial applications, typically in conjunction with spray drying processes. In a two-fluid nozzle, a low-velocity liquid stream encounters a high-velocity gas stream that generates high shear forces to accomplish atomization of the liquid. A direct result of this interaction is that the droplet size characteristics of the aerosol are dependent on the relative mass flow rates of the liquid precursor and nozzle gas stream. The velocity of the droplets as they leave the generation zone can be quite large which may lead to unacceptable losses due to impaction. The aerosol also leaves the nozzle in a characteristic pattern, typically a flat fan, and this may require that the dimensions of the reactor be sufficiently large to prevent unwanted losses on the walls of the system.

Thus, a variety of atomization techniques for spray processing methods are possible for modified carbon production and different versions are preferred for different feed streams and products.

The atomized suspension must be heated to remove solvents and react the diazonium salt. For example, a horizontal, tubular hot-wall reactor can be used to heat a gas stream to a desired temperature. Energy is delivered to the system by maintaining a fixed boundary temperature at the wall of the reactor and the maximum temperature of the gas is the wall temperature. Heat transfer within a hot wall reactor occurs through the bulk of the gas. Buoyant forces that occur naturally in horizontal hot wall reactors aid this transfer. The mixing also helps to improve the radial homogeneity of the gas stream. Passive or active mixing of the gas can also increase the heat transfer rate. The maximum temperature and the heating rate can be controlled independent of the inlet stream with small changes in residence time. The heating rate of the inlet stream can also be controlled using a multi-zone furnace.

The use of a horizontal hot-wall reactor according to the present invention is preferred to produce particles with a size of not greater than about 5 µm. Above about 5 µm, settling of particles can cause significant material losses. One disadvantage of such reactors is the poor ability to atomize particulate carbons when using submerged ultrasonics for atomization.

Alternatively, the horizontal hot-wall reactor can be used with a two-fluid nozzle to atomize the droplets. This approach is preferred for precursor feed streams containing relatively high levels of carbon. A horizontal hot-wall reactor can also be used with ultrasonic nozzle atomization techniques. This allows atomization of precursor containing particulate carbons; however the large droplet size leads to losses of materials on reactor walls and other surfaces making this an expensive method for powder production.

While horizontal hot-wall reactors are useful according to the present invention, spray processing systems in the configuration of a spray dryer are the generally preferred production method for large quantities of modified carbon powders that are useful in accordance with the present invention.

Spray drying is a process wherein powders are produced by atomizing a precursor to produce droplets and evaporating the liquid to produce a dry aerosol, wherein thermal decomposition of one or more precursors (e.g., a diazonium salt) may take place to produce the powder. The residence time in the spray dryer is the average time the process gas spends in the drying vessel as calculated by the vessel volume divided by the process gas flow using the outlet gas conditions. The peak excursion temperature (i.e., the reaction temperature) in the spray dryer is the maximum temperature of a particle, averaged throughout its diameter, while the particle is being processed and/or dried. The droplets are heated by supplying a pre-heated carrier gas.

Three types of spray dryer systems are useful for spray drying to form modified carbon products according to the present invention. An open system is useful for general spray drying to form powders using air as an aerosol carrier gas and an aqueous feed solution as a precursor. A closed system is useful for spray drying to form powders using an aerosol carrier gas other than air. A closed system is also useful when using a non-aqueous or a semi-non-aqueous solution as a precursor. A semi-closed system, including a self-inertizing system, is useful for spray drying to form modified carbon powders that require an inert atmosphere and/or precursors that are potentially flammable.

In addition, two spray dryer designs are particularly useful for the production of modified carbon products. A co-current spray dryer is useful for production of modified carbon products that are sensitive to high temperature excursions (e.g., greater than about 350° C.) or that require a rotary atomizer to generate the aerosol. Mixed-flow spray dryers are useful for producing modified carbon powders that require relatively high temperature excursions (e.g., greater than about 350° C.) or require turbulent mixing forces. According to the present invention, co-current spray-drying is preferred for the manufacture of modified carbon black products.

In a co-current spray dryer, the hot gas is introduced at the top of the unit where the droplets are generated with any of the atomization techniques mentioned above. The maximum temperature that a droplet/particle is exposed to in a co-current spray dryer is the temperature of the outlet. Typically, the outlet temperature is limited to about 200° C., although some designs allow for higher temperatures. In addition, since the particles experience the lowest temperature in the beginning of the time-temperature curve and the highest temperature at the end, the possibility of precursor surface diffusion and agglomeration is high.

These conditions are advantageous for modified carbon particle synthesis at a wide range of diazonium salt (surface functional group) loadings, such as up to about 5 µmol/m$^2$ surface functional groups on carbon. For co-current spray dryers the reaction temperatures can be high enough for the reaction of the diazonium salt (e.g., between 25° C. and 100° C.).

A mixed-flow spray dryer introduces the hot gas at the top of the unit and the precursor droplets are generated near the bottom and are directed upwardly. The droplets/particles are forced towards the top of the unit then fall and flow back down with the gas back down, increasing the residence time in the spray dryer. The temperature the particles experience is also higher as compared to a co-current spray dryer.

The highest temperature in these spray dryers is the inlet temperature (e.g., 180° C.), and the outlet temperature can be as low as 50° C. Therefore, the modified carbon particles reach the highest temperature for a relatively short time, which advantageously reduces migration or surface diffusion of the surface groups. This spike of high temperature can quickly convert the diazonium salt and is followed by a mild quench since the spray dryer temperature quickly decreases after the maximum temperature is achieved. Thus, the spike-like temperature profile can be advantageous for the generation of highly dispersed modifying groups on the surface of the carbon.

The range of useful residence times for producing modified carbon products depends on the spray dryer design type, atmosphere used, nozzle configuration, feed liquid inlet temperature and the residual moisture content. In general, residence times for the production of modified carbon powders can range from 5 seconds up to 5 minutes.

For a co-current spray-drying configuration, the range of useful inlet temperatures for producing modified carbon products depends on a number of factors including solids loading and droplet size, atmosphere used and energy required to perform drying and/or reaction of the diazonium salt. Useful inlet temperatures should be sufficiently high to accomplish the drying and/or reaction of the diazonium salt without promoting significant surface diffusion of functional groups to reduce its performance.

In general, the outlet temperature of the spray dryer determines the residual moisture content of the powder. For example, a useful outlet temperature for co-current spray drying according to one embodiment of the present invention ranges from about 50° C. to about 80° C. Useful inlet temperatures, according to the present invention, range from about 130° C. to 180° C. The carbon solids loading can be up to about 50 wt. %.

Other equipment that is desirable for producing modified carbon products using a spray dryer includes a heater for the gas and a collection system. Either direct heating or indirect heating, including burning fuel, heating electrically, liquid-phase heating or steam heating, can accomplish heating of the gas. Many collection methods are useful for collecting modified carbon powders produced on a spray dryer. These methods include, but are not limited to those using cyclone, bag/cartridge filter, electrostatic precipitator, and various wet collection techniques.

A particularly preferred spray process for producing carbon-based products is disclosed in commonly-owned U.S. Pat. No. 6,660,680 by Hampden-Smith et al., which is incorporated herein by reference in its entirety.

Another embodiment of the current invention is the use of spray-based processing, as described above, to produce, in one step, metal-functionalized modified carbon products. Here, a metal-containing species is added to the carbon/diazonium precursor medium prior to spray-processing. In a related embodiment, the modified carbon products are metal-functionalized by spray-based processing where the precursor contains modified carbon products (previously produced) and metal-containing species.

The present invention is based upon the metal-functionalization of surface modified carbon products. Carbon products can be modified on their surface to contain covalently bonded surface organic moieties that exhibit a wide range chemical and physical properties. These organic moieties can be further functionalized by reaction with metal-containing species to form metal-functionalized carbon products where a metal species is either ionically or covalently bonded to the surface organic group.

The organic moieties created on the surface of the carbon products can be used to interact with metal species to form what is referred to herein as metal-functionalized carbon products. There are two general classes of metal-functionalized carbon. The first type is a carbon material that is functionalized with metal ions that are relatively weakly coordinated to the surface functional group. These metal ions are typically relatively easily exchanged and in general impart an ion-exchange functionality to the material. The second class of metal-functionalized carbons includes metal species that are coordinated in a more covalent fashion to create a surface bound coordination complex. These metals are typically less easily exchangeable and are coordinated in a more rigid ligand environment, and impart a functionality that is based on having a metal species coordinated in a particular environment on the surface, such as catalysis, molecule-specific adsorption, luminescence and the like; or the coordinated metal complex can act as a precursor to a reduced metal species, typically metal nanoparticles that are dispersed over the surface of the support phase. As anyone skilled in the art will appreciate, the extent of ionic versus covalent binding of metal species varies widely and this classification is intended for the convenience of organizing the function and applications of these metal-functionalized materials.

In one embodiment of the present invention, where the metal species to be bound are required to exist in an ionic form, the surface functional group is typically easily ionizable. Examples of these groups include sulfonic acids, e.g. $-SO_3^-$, $-PO_3^{2-}$ and $-NH_3^+$. The metal group may be in the form of a discrete or hydrated metal ions such as $Li^+$, $K^+$, $Na^+$, $Ca^{2+}$ or $Mg^{2+}$ as depicted FIG. 3. In the case where the metal is bound in a stronger covalent state to form a coordination compound, the surface functional group should contain an electron pair donor such as $-NR_2$, $-CO_2^-$ or $-SR$. In this case, the metal group formed is a coordination complex where the surface functional group may be neutral (e.g., $-NR_2$, $-SR$) or may be charged such as $-CO_2^-$. Other ligands may also be present in the coordination sphere of the metal ion to satisfy the coordination number of the species such as nitrogen donors (e.g., amines), phosphorus donors (e.g., phosphines), sulfur donors (e.g., thiols), or oxygen donors such as alcohols, ketones, aldehydes and carboxylic acids. In addition, combinations of these two situations may occur where coordination compounds may be bound to the carbon surface via the organic functional moiety which are also charged, either anionically or cationically, or an ionic species may be more covalently bonded.

The foregoing classification can be used to organize the functionality of these metal-functionalized carbons and as a result, their applications. For example, the metal groups that are intentionally ionically bonded can be bonded in a reversible fashion, where the strength of binding can be controlled by the ligand environment and the trigger for binding reversal can be influenced by an external stimulus such as pH, electrical stimulation, change in concentration, or the like. This results in applications where ionic conductivity and ion separation are critical such as in lithium ion batteries, electrodialysis, sensing, and the like. There are also a number of related applications where the metal groups may be tightly bound to the modified carbon, but where a ligand within its coordination sphere is reversibly bound, for example, where the ligand is an ionic species such as hydroxide ion that is the basis of the operation of electrochemical capacitors.

The more covalently bonded metal species, are those that are typically bound strongly to the surface modified carbon and the ligand environment of that metal group is controlled to be either: highly static—to achieve, for example, chiral catalysis; or highly dynamic—to achieve reversible adsorption of specific molecules (ligands). These metal functionalized carbon species can be used for a variety of applications that vary from catalysis, molecular imprinting, specific gas adsorption and reversible gas storage, where the metal species remains intact on the surface. They can also be used in applications where the metal group acts as a precursor to metal or metal-containing (e.g., metal oxide, nitride, halide or sulfide) materials by conversion at relatively low temperatures. These metal-functionalized materials are valuable in applications where highly dispersed metal or metal-containing nanoparticles are required to be dispersed over a high surface area support or a continuous phase derived from conversion of the metal species is required in the final product. Application areas of these materials according to the present invention include heterogeneous catalysts and electrocatalysts, as well as electronic conductors.

The metal-functionalized carbon materials may be prepared by a number of approaches. For example, a metal complex can be reacted with the surface functional groups of surface modified carbon in a liquid medium (including aqueous or non-aqueous solvents) by contacting the surface modified carbon product with a dissolved or suspended metal-containing reagent. In the case where the modified carbon product is a particulate material, a dispersion of the modified carbon black can be stirred while in contact with the metal-containing reagent, heated if necessary and the metal functionalized product can separated from the reaction medium. The analogous reaction may also be carried out in the gas phase wherein the modified carbon particles can be fluidized in either a static or moving fluidized bed and contacted with a gaseous metal-containing reagent. The same result can also be achieved in a batch type process where a modified carbon powder batch is infiltrated with a vapor phase reagent.

In the case where the modified carbon product is not particulate, but is a fiber-based material such as a woven or non-woven carbon cloth or paper, it can be contacted with the metal-containing reagent in the liquid or gas phase on a continuous basis to form the metal-functionalized product.

In another embodiment of the present invention, the metal-functionalized product that has been functionalized with a metal-containing molecule or complex (i.e., a metal group), can be converted to a metal-based product (such as a metal, metal oxide, metal nitride and the like) particles by thermal, chemical, photochemical or electrochemical conversion. One method for thermal conversion includes spraying a liquid containing a metal-molecule functionalized carbon suspension into a furnace to convert the metal-molecule into a metal-based species, if necessary in the presence of other reagents to form metal oxides, borides, nitrides etc. as is described in U.S. Pat. No. 6,338,809 by Hampden-Smith et al., which is incorporated herein by reference in its entirety.

According to one embodiment of the present invention, the modified carbon products are used in electronic applications. The functionality that is required for these metal-functionalized carbon products is that the products be electronically conductive. The metal-functionalized carbon product can be conductive with or without a post-processing step like, for example, exposure to elevated temperature or a reductive atmosphere. It is also preferred that the products exhibit the maximum electrical conductivity at the lowest cost, which typically means with the least amount of metal. In this embodiment of the invention, electrical conductivity is achieved by forming an intermediate metal functionalized carbon in which the metal that is bound to the modified carbon surface is one that can be converted to a zero valent metal species where the metal species is highly conductive. The metal functionalized carbons according to this embodiment are preferably complexes of silver(I), copper(I) or copper(II) or nickel(II) that can be converted to metallic silver, copper or nickel, respectively. The advantage in coordinating these metal ions to the surface of the modified carbon products as compared to making a mixture of carbon and metal particles or a mixture of carbon particles and metal complexes, is that the final zero valent metal is distributed over the surface of the carbon product, which enables the best electrical conductivity at the lowest mass and volume fraction of the zero valent metal. However, in order to increase the metal content of these metal-functionalized carbon products it is also an aspect of the present invention that additional metal species can be added. The metal species can be in the form of an additional amount of metal complex, zero valent metal that may be in the form of metal nanoparticles, micro-sized metal particles or metal flakes.

Figure 4:
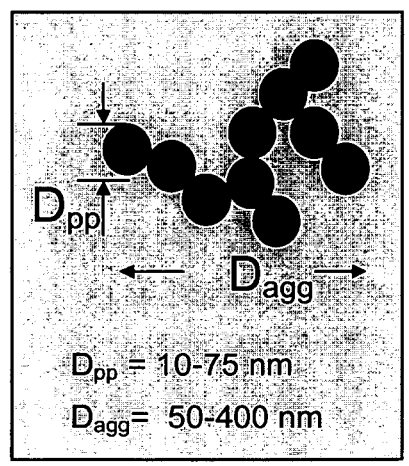
FIG. 4 illustrates the structure of carbon black.
Figure 4:
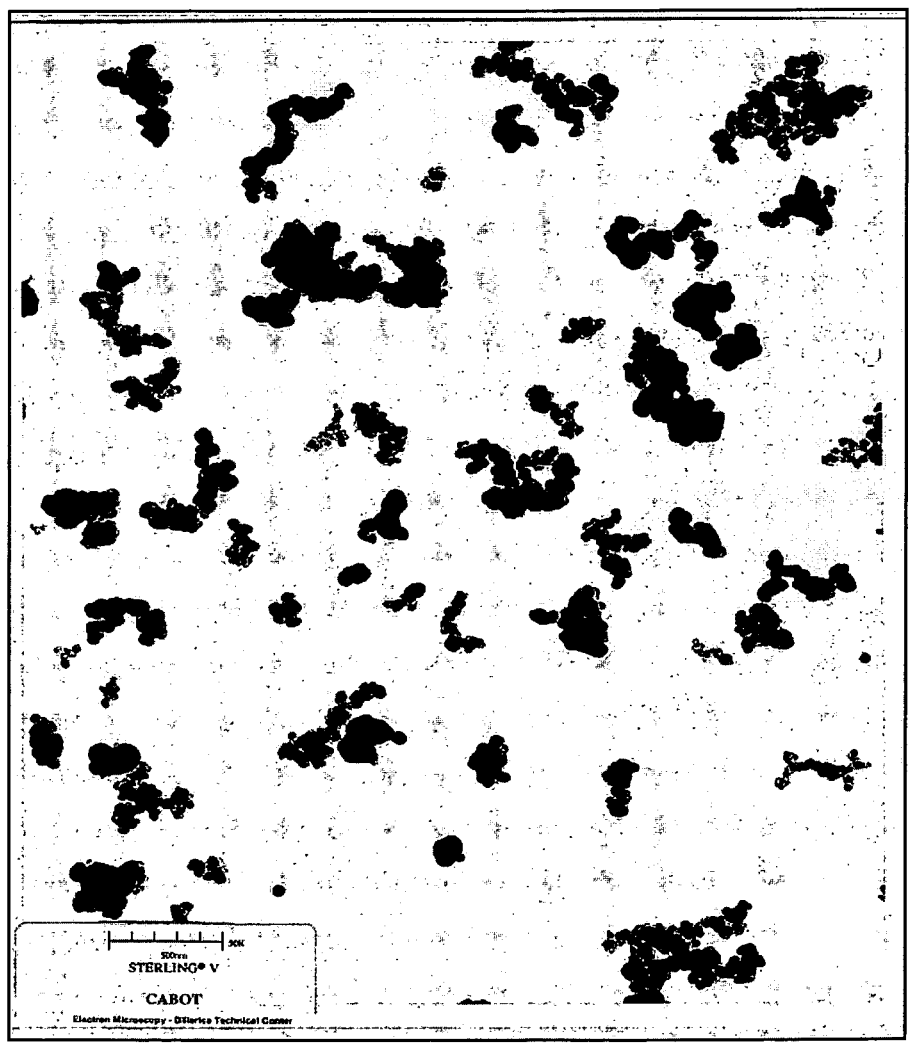

The metal-functionalized carbon product can include carbon particles, such as VULCAN XC-72 (a carbon black available from Cabot Corp., Boston, Mass.) which is comprised of smaller substantially spherical particles that range in size from 10 to 75 nm and which are typically agglomerated into aggregates that range in size from 50 to 400 nm. A typical example of these particles is illustrated in FIG. 4.

Figure 5:
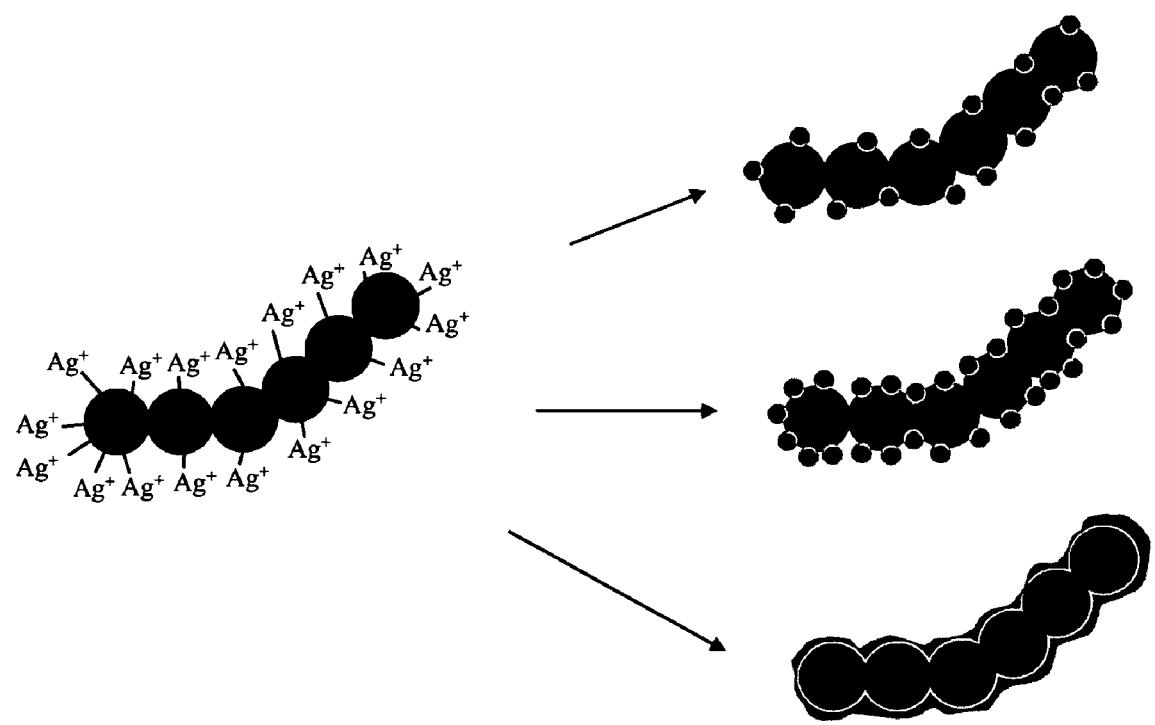
FIG. 5 illustrates silver-bound carbon black and conversion to carbon-silver nanocomposites of varying microstructure according to the present invention.
Figure 6:
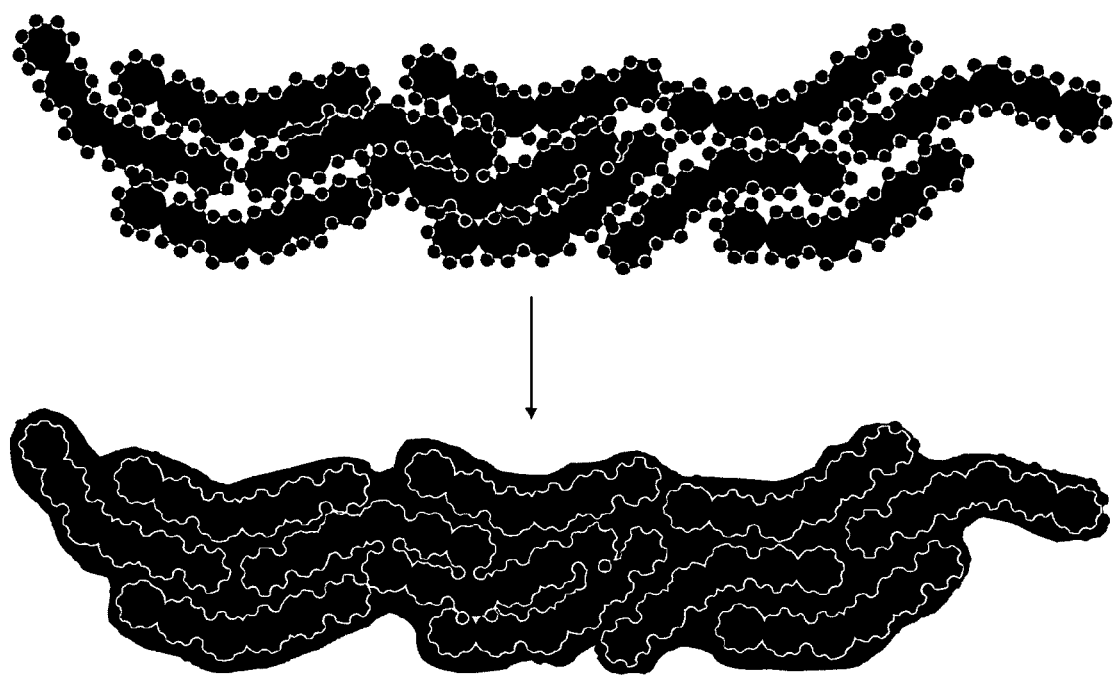
FIG. 6 illustrates the conversion of a silver-carbon nanocomposite to a conductive silver-carbon macrocomposite according to the present invention.

These carbon aggregates can be metal functionalized with a metal, for example, silver. The concentration and distribution of silver ions bound to the surface of the carbon particles can be controlled through the number and type of surface functional groups. The coordinated silver compounds can be converted to silver metal either prior to printing onto a surface or after printing onto a surface. Some examples of the structures that can be produced are shown in FIGS. 5 and 6. At low metal ion concentrations, highly dispersed metal nanoparticles are formed on the surface of the carbon aggregates, while at higher concentrations, metal-coated carbon aggregates are formed. When attempting to form a conductive layer derived from these silver-coated carbon aggregates, it may only be necessary to form a high concentration of dispersed silver nanoparticles on the surface which is stable in an ink or paste dispersion because as multiple aggregates come together, the nanoparticles can react and sinter at relatively low temperature to form a conductive metal path. This approach avoids the issues of having dispersed metal nanoparticles that are highly mobile in an ink or paste and which will react with each other to form larger particles and precipitate if not surface passivated. However, the fact that they are passivated can adversely affect the process parameters of these materials when they are converted into a metallic feature because the surface passivating groups must now be removed.

According to a further embodiment of the present invention, by using aggregated carbon nanoparticles the primary carbon aggregates are already necked and therefore limit the deposition of metal where the metal is not useful. This reduces the mass of metal that is required to make a conductive layer.

Figure 7:
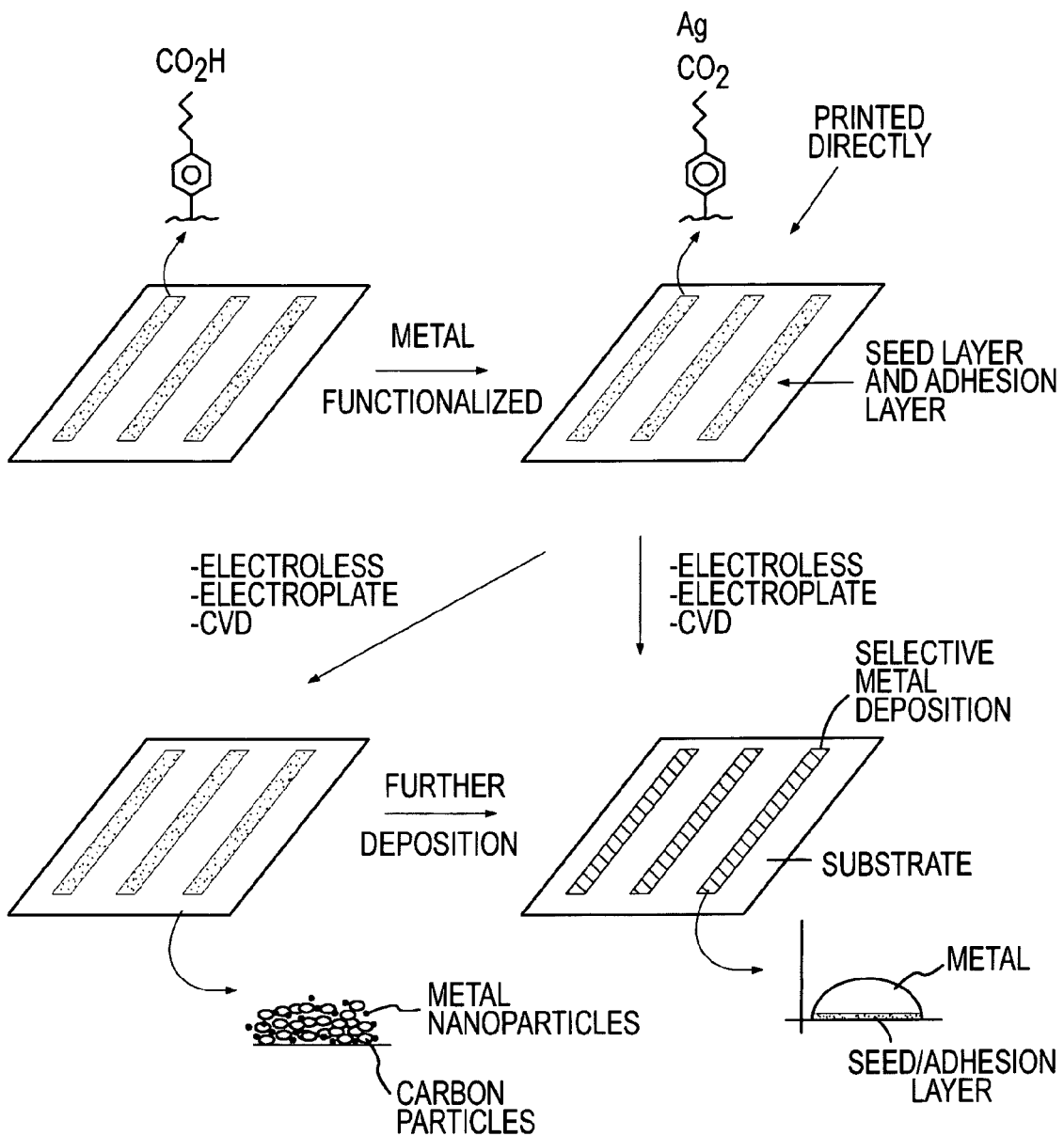
FIG. 7 illustrates schematic for conductor formation via metal-functionalized modified carbon products according to the present invention.
Figure 8:
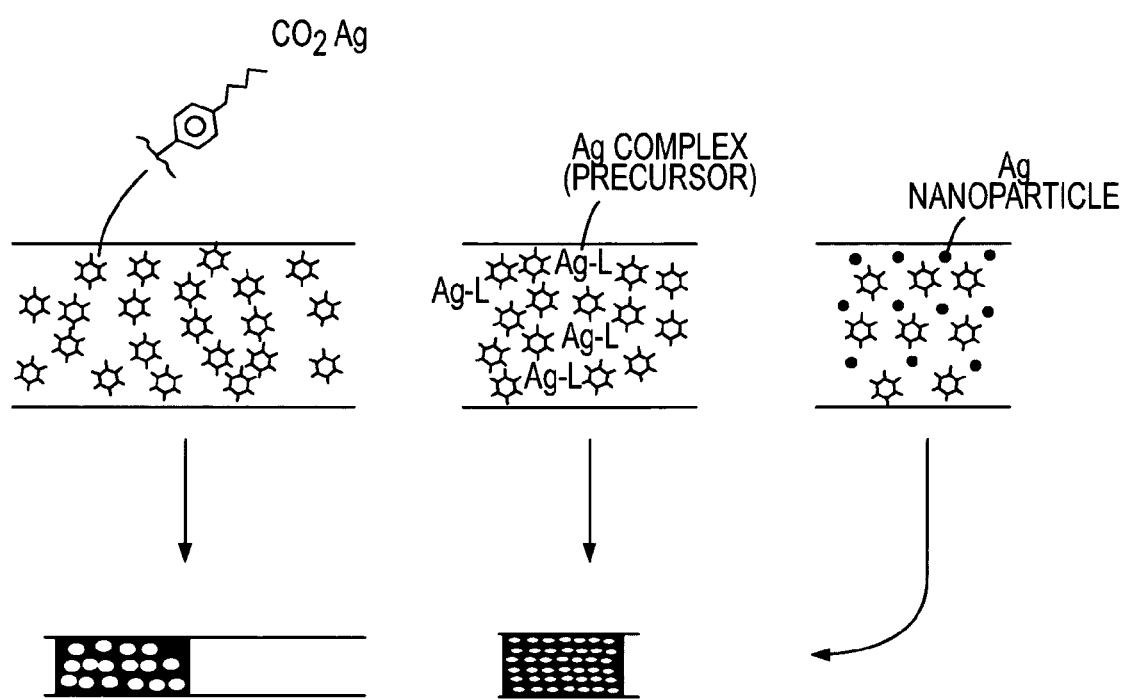
FIG. 8 illustrates schematic for conductor formation via metal-functionalized modified carbon products where metal-functionalized modified carbon black is mixed with additional metal compounds or metal nanoparticles.

According to another embodiment of the present invention, the modified carbon products are dispersible in an ink or a paste such that they can be printed or coated onto a surface and subsequently converted into a carbon-filled metallic feature, as depicted in FIGS. 7 and 8. Depending on the printing or coating process and the conductor attributes required, the ink or paste may or may not have additional silver containing compounds or silver nanoparticles and the ink or pastes that are comprised of metal-functionalized carbon will have different characteristics of viscosity, shelf life and composition. Organically functionalized carbon particles have been disclosed by Belmont et al. to be stable in inks at relatively high loading for ink-jet printing. Metal-functionalized carbons, particularly where the metal ion is monovalent, are also stable in inks at relatively high loading resulting in low viscosity inks suitable for a variety of analog and digital printing techniques including but not limited to lithographic, flexographic, xerographic, electrostatic, gravure, spray, syringe and ink-jet printing. The inks suitable for digital printing, including ink-jet printing, often contain other species such as humectants to avoid drying out of the ink in the ink-jet print head. For other coating methods such as offset, lithographic, gravure or screen printing, to achieve a blanket layer or a patterned structure, higher viscosity pastes are generally required and often the hydrophilic nature of the inks should be controlled to allow for controlled wetting of a printing plate. These inks and pastes may also contain other components such as rheology modifiers. These inks or pastes may also contain further amounts of metal complexes or metallic particles such as nanoparticles or flakes depending upon the nature of the ink or paste and the desired printing process. For example, in order to produce a stable low viscosity ink for ink-jet printing that can be converted to a highly conductive carbon filled silver feature, the silver functionalized carbon particles in the ink can be mixed with silver nanoparticles which are also stabilized by organic groups on the surface of the carbon particles or by other components in the suspension.

As a further embodiment of the present invention, the metal-functionalized carbons can be converted to zero valent metallic phases at low temperatures. This low temperature conversion enables the printing or coating of substrates such as papers and plastics (such as polyester and the like) that are temperature sensitive. In this embodiment of the invention, the organic moiety should be chosen such that it can lead to conversion (reduction) of the coordinated metal species at low temperature through thermal, photochemical or chemical means. As an example of chemical conversion, it is well known that carboxylate derivatives of silver(I) can be thermally converted to silver metal at relatively low temperatures such as between 50° C. and 150° C. The metal-functionalized carbon product should be thermally stable under ambient conditions to avoid premature conversion to silver prior to being printed onto a surface. Other types of chemical reactions can be thermally induced. For example, copper metal can be formed from the disproportionation of copper(I) complexes to form copper metal and copper(II). The copper(II) can be removed from the system or can be further converted into copper metal by reduction.

Another method by which the metal-functionalized carbons can be converted to metal at low temperature is by irradiation with suitable wavelength light. In the case of silver compounds, the silver(I) complex and its surrounding ligands comprises the chromophore and upon irradiation with ultraviolet light the silver(I) compound is reduced to silver metal.

In another embodiment according to the present invention, the metal species in the metallized carbons can be chemically reduced to metal by reaction with a reducing agent such as hydrogen, a metal hydride, alcohol, aldehydes, ketones and the like.

According to another embodiment of the present invention, the metal-functionalized carbon species may be designed to act as a catalyst for the reaction of other species on the surface of the carbon particles to form a metallic coating. For example, metal-functionalized carbon particles may be deposited onto a surface in a pattern by any one of the printing approaches described above. The metal functionalization acts as a catalyst to react with a source of metal containing species to form a coating over the surface of the metal functionalized carbon. This may be achieved by a number of deposition methods including solution-based methods such as electrodeposition, underpotential deposition or electroless deposition, or this can be achieved by vapor-phase deposition methods such as chemical vapor deposition, where the metal-functionalized carbon acts as a nucleation site for deposition and growth of the layer. In this particular embodiment, the metal functionalization can also be formed by a vapor phase process where the volatile metal-containing molecule reacts with the surface organic moiety to initially form a metal functionalized carbon, which subsequently reacts to form metal and acts as nucleation sites for further deposition.

As a further embodiment of this aspect of the invention, redox active materials can be incorporated to ensure reduction of the oxidized metallic species to the final reduced metal phase. For example, a first metal ion may coordinate to the surface of the functionalized carbon particles and a second metal species may be added to the system. As the first metal species is reduced to metal by, for example, a thermal or a photochemical process, this reduced first metal species can act as a reducing agent for the second metal. On reducing the second metal from an oxidized metal species to the reduced metallic form, the first metal is again re-oxidized and further reduces additional amounts of the second metal species.

According to a further embodiment of the present invention, the carbon particles used to support the metallic species have a high absorption cross-section in the infra-red range leading to good thermal absorbtivity. This is important in applications where thermal conversion of the metal-functionalized carbons are required in the presence of other temperature sensitive materials such as polymer substrates, which are likely to have a lower absorption cross section (and therefore become less hot).

According to another embodiment of the present invention, the surface modified carbon products can be used in Atomic Layer Deposition (ALD) processes through sequential introduction of reagents that are chemically matched to the carbon surface for compositionally and dimensionally controlled surface coatings. As an example, a surface modified carbon product such as a sulfonyllic acid or carboxylic acid terminated surface can be reacted with a metal compound such as a metal amide such as $Ti(NR_2)_4$. After reaction, the surface confined titanium compound can be reacted with, e.g., ammonia and subsequently heat treated to form TiN. The Ti reagent and then the ammonia reagent can be sequentially reacted in subsequent cycles to deposit layers with molecular level control over deposit thickness and composition. A wide variety of metal oxide, nitride, sulfide and carbide surface coatings can be constructed in this manner.

According to another embodiment of the present invention, multiple organic moieties can be present on the surface of the carbon products where each organic moiety has a different functionality. For example, one surface organic group may serve to bind the metal ion of choice while others are present to ensure other characteristics such as hydrophobicity, hydrophilicity, reducing properties, and the like.

According to a further embodiment of the present invention, using mutli-functional organic species such as polycarboxlates or polysulfonic acids can increase the metal loading of the metal-functionalized carbon materials. As an example, 4 μmol of surface functional groups on a carbon product that has a surface area of 600 $m^2/g$ is equivalent to about 26 wt. % silver if each surface organic group can coordinate one silver ion. If there are 3 functional groups for each surface modification group, then the silver weight loading is increased to 75 wt. %.

The modified carbon suspensions according to the present invention can be deposited to form patterned or unpatterned layers using a variety of tools and methods. As used herein, a direct-write deposition tool is a device that deposits a liquid or liquid suspension onto a surface by ejecting the composition through an orifice toward the surface without the tool being in direct contact with the surface. The direct-write deposition tool is preferably controllable over an x-y grid. A preferred direct-write deposition tool according to the present invention is an ink-jet device. Other examples of direct-write deposition tools include aerosol jets and automated syringes, such as the MICROPEN tool, available from Ohmcraft, Inc., of Honeoye Falls, N.Y.

Ink-jet devices operate by generating droplets of the suspension and directing the droplets toward a surface. The position of the ink-jet head is carefully controlled and can be highly automated so that discrete patterns of the modified carbon product can be applied to the surface. Ink-jet printers are capable of printing at a rate of 1000 drops per second per jet, or higher, and can print linear features with good resolution at a rate of 10 cm/sec or more, such as up to about 1000 cm/sec. Each drop generated by the ink-jet head includes approximately 25 to 100 picoliters of the suspension which is delivered to the surface. For these and other reasons, ink-jet devices are a highly desirable means for depositing materials onto a surface.

Typically, an ink-jet device includes an ink-jet head with one or more orifices having a diameter of not greater than about 100 μm, such as from about 50 μm to 75 μm. Droplets are generated and are directed through the orifice toward the surface being printed. Ink-jet printers typically utilize a piezoelectric driven system to generate the droplets, although other variations are also used. Ink-jet devices are described in more detail in, for example, U.S. Pat. No. 4,627,875 by Kobayashi et al. and U.S. Pat. No. 5,329,293 by Liker, each of which is incorporated herein by reference in their entirety.

It is also important to simultaneously control the surface tension and the viscosity of the modified carbon suspensions to enable the use of industrial ink-jet devices. Preferably, the surface tension is from about 10 to 50 dynes/cm, such as from about 20 to 40 dynes/cm. For use in an ink-jet, the viscosity of the modified carbon suspensions is preferably not greater than about 50 centipoise (cp), such as in the range of from about 10 cp to about 40 cp. Automated syringes can use compositions having a higher viscosity, such as up to about 5000 cp.

According to one embodiment, the solids loading of particles in the modified carbon suspensions is preferably as high as possible without adversely affecting the viscosity or other necessary properties of the composition. For example, a modified carbon suspension can have a particle loading of up to about 20 wt. %, and in one embodiment the particle loading is from about 2 wt. % to about 8 wt. %. As is discussed above, the surface modification of the carbon product can advantageously enhance the dispersion of the carbon product, and lead to higher obtainable solids loadings.

The modified carbon suspensions for use in an ink-jet device can also include water and an alcohol. Surfactants can also be used to maintain the particles in suspension. Co-solvents, also known as humectants, can be used to prevent the modified carbon suspensions from crusting and clogging the orifice of the ink-jet head. Biocides can also be added to prevent bacterial growth over time. Examples of such liquid vehicle compositions for use in an ink-jet are disclosed in U.S. Pat. No. 5,853,470 by Martin et al.; U.S. Pat. No. 5,679,724 by Sacripante et al.; U.S. Pat. No. 5,725,647 by Carlson et al.; U.S. Pat. No. 4,877,451 by Winnik et al.; U.S. Pat. No. 5,837,045 by Johnson et al.; and U.S. Pat. No. 5,837,041 by Bean et al. Each of the foregoing U.S. patents is incorporated by reference herein in its entirety. The selection of such additives is based upon the desired properties of the composition. Modified carbon particles can be mixed with the liquid vehicle using a mill or, for example, an ultrasonic processor.

The modified carbon suspensions according to the present invention can also be deposited by aerosol jet deposition. Aerosol jet deposition can enable the formation of modified carbon features having a feature width of not greater than about 200 µm, such as not greater than 100 µm, not greater than 75 µm and even not greater than 50 µm. In aerosol jet deposition, the modified carbon suspension is aerosolized into droplets and the droplets are transported to the substrate in a flow gas through a flow channel. Typically, the flow channel is straight and relatively short. For use in an aerosol jet deposition, the viscosity of the suspension is preferably not greater than about 20 cp.

The aerosol can be created using a number of atomization techniques. Examples include ultrasonic atomization, two-fluid spray head, pressure atomizing nozzles and the like. Ultrasonic atomization is preferred for compositions with low viscosities and low surface tension. Two-fluid and pressure atomizers are preferred for higher viscosity suspensions.

The size of the aerosol droplets can vary depending on the atomization technique. In one embodiment, the average droplet size is not greater than about 10 µm and more preferably is not greater than about 5 µm. Large droplets can be optionally removed from the aerosol, such as by the use of an impactor.

Low aerosol concentrations require large volumes of flow gas and can be detrimental to the deposition of fine features. The concentration of the aerosol can optionally be increased, such as by using a virtual impactor. The concentration of the aerosol can be greater than about $10^6$ droplets/cm$^3$, such as greater than about $10^7$ droplets/cm$^3$. The concentration of the aerosol can be monitored and the information can be used to maintain the mist concentration within, for example, 10% of the desired mist concentration over a period of time.

Examples of tools and methods for the deposition of fluids using aerosol jet deposition include U.S. Pat. No. 6,251,488 by Miller et al., U.S. Pat. No. 5,725,672 by Schmitt et al. and U.S. Pat. No. 4,019,188 by Hochberg et al. Each of these U.S. patents is incorporated herein by reference in their entirety.

The modified carbon product suspensions and metal functionalized modified carbon product suspensions of the present invention can also be deposited by a variety of other techniques including intaglio, roll printer, spraying, dip coating, spin coating and other techniques that direct discrete units, continuous jets or continuous sheets of fluid to a surface. Other printing methods include lithographic and gravure printing.

For example, gravure printing can be used with modified carbon suspensions having a viscosity of up to about 5000 centipoise. The gravure method can deposit features having an average thickness of from about 1 µm to about 25 µm and can deposit such features at a high rate of speed, such as up to about 700 meters per minute. The gravure process also enables the direct formation of patterns onto the surface.

Lithographic printing methods can also be utilized. In the lithographic process, the inked printing plate contacts and transfers a pattern to a rubber blanket and the rubber blanket contacts and transfers the pattern to the surface being printed. A plate cylinder first comes into contact with dampening rollers that transfer an aqueous solution to the hydrophilic non-image areas of the plate. A dampened plate then contacts an inking roller and accepts the ink only in the oleophillic image areas.

According to another embodiment of the present invention, the functional groups covalently attached to the carbon product are selected such that they interact with metal ions to reversibly bind to the metal ions. The target ions that are bound can preferably be chosen from protons ($H^+$), the alkali and alkali earth metals, the transition elements, and the elements of Groups 13, 14 and 15 of the periodic table. The reversible nature of the metal ion binding enables transport and/or storage of these ions or separation of these ions through a membrane. For example, for lithium ion batteries, it is desirable to use a separator that selectively and reversibly transports lithium ions ($Li^+$) between the electrodes. A composite lithium ion transport separation membrane can include a lithium ion functionalized carbon material (e.g., carbon particles, fibers or cloth) imbedded in a polymer matrix to form a separation membrane. In addition, one problem associated with lithium ion batteries is the reversible uptake of lithium during the charging cycle. During charging of the battery, lithium is removed from the cathode and is intercalated into the graphite anode. However, the capacity for the reversible uptake of lithium into the graphite anode typically degrades over time. According to the present invention, funtionalization of the graphite in the anode with a functional group that reversibly binds lithium ions can provide a mechanism for enhanced capacity of lithium in the anode.

According to another embodiment of the present invention, the modified carbon products are used in electrodialysis and other membrane applications. Electrodialysis is an ion separation process that relies on the transport of ions through ion permeable membranes under the influence of an electrical potential gradient. It finds a variety of applications including water desalination and deionization, production of chlorine, acids and bases, and chemical syntheses involving ions selectively transported through the ion-exchange membranes (see, for example, Grebenyuk et al., *Russ. J. Electrochem.*, 38, pp. 806-809 (2002)). Additional information on the application of electrodialysis in the purification of wastewaters from ionic impurities such as the demineralization of whey, and the clean-up of electroplating wastewater can be found in Bodzek, "Water Management, Purification & Conservation in Arid Climates", Lancaster, pp. 121-183.

The process is similar to electrolysis, in which ionic species in a solution migrate towards the poles of opposite charge. The addition of one or more ion-selective membranes in the system enables the separation of ions in distinct channels and is the key to the successful implementation of this process.

The process has various shortcomings, which are mostly related to the membrane properties. Some of the requirements for electrodialysis membranes are listed in "Perry's Chemical. Engineering Handbook", pp. 22-42 to 22-48. The membranes should have physical and mechanical stability, should be inert to changes in the ionic strength of the solution and should tolerate thermal stresses. In addition they should be stable to pH extremes and be capable of withstanding the entire pH range between pH 0 and pH 14. The membranes should also have low electrical resistance since they operate inside an electric field.

Traditionally, ion-exchange membranes that are utilized in electrodialysis systems are manufactured from polymeric materials. The important performance parameters of these membranes can be tailored by varying the properties of the polymers, such as cross-link density and ion capacity. However, manufacturers typically encounter situations where the improvement in one property of the membrane leads to the deterioration of another equally important property. For example, increasing the charge density of the membrane enhances its selectivity and reduces its electrical resistance, but leads to increased swelling and reduced mechanical stability. As a consequence, electrodialysis membrane manufacturers are forced to compromise to a sub-optimal membrane composition.

The incorporation of carbonaceous or other electrically conductive materials into ion-exchange membranes has been explored in the past as a way to enhance the mechanical stability of the membranes without compromising the electrical resistance. For example, Hodgdon et al. in U.S. Pat. No. 4,505,797 describe an ion exchange membrane reinforced with non-woven carbon fibers that has reduced electrical resistance. Goldstein in U.S. Pat. No. 4,216,073 describes the use of an ion exchange resin in membrane form that includes activated carbon to prevent fouling. Bahar et al., in U.S. Reissue Pat. No. Re 37,701 describe a composite membrane consisting of a mixture of ion exchange materials and finely divided powders selected from a wide range of organic and inorganic compounds, including carbon black, graphite, nickel, silica, and platinum black to impart effects such as color, electrical and/or thermal conductivity, catalytic effects or certain reactant transport properties to the membrane.

According to the present invention, modified carbon products can be incorporated into electrodialysis membranes or other composite membranes over a wide range of loadings. The incorporation of these materials can significantly enhance the performance of the membranes in at least the following ways:

1. Increase the base electrical and thermal conductivity of the membrane since the base carbon particles are inherently electrically and thermally conductive.
2. Increase the mechanical stability of the membrane by incorporating carbonaceous rigid structures, such as carbon black particles, carbon fibers, carbon cloths and graphite flakes. Functional groups can be attached to the carbonaceous particles that improve their compatibility with the polymer constituents of the membrane enabling better dispersion of the particles in the membrane composite.
3. Increase the chemical stability of the membrane with respect to aggressive acidic or basic chemical environments by including surface modified carbonaceous compounds that are pH stable.
4. Reduce membrane swelling by substituting rigid modified carbon products such as carbon particles that have one or more ionic groups attached to the particles for the swellable polymer ion-exchange groups. Surface modified carbonaceous particles can be prepared with one or more anionic groups, e.g., benzenesulfonic acid, benzoic acid, etc. or cationic groups (phenyl pyridinium, phenethylamine, etc.) attached to the surface to have flexible chemistry that can be applied to both cation and anion exchange electrodialysis membranes.
5. Enhance the selectivity of the membrane by incorporating modified carbon products with functional groups that promote selective adsorption or transport. The choice of surface group can impact the mobility of the ions that are transported through the membrane. For example, acidic groups with chelating properties can be used to immobilize or decrease the mobility of multivalent metal cations, while selectively permitting the transport of monovalent cations through the membrane. Also, groups can be attached to the surface to selectively immobilize other ionic components that may need to be separated from the bulk of the ions, thus leading to concentrated acids and bases.
6. Enhance the catalytic activity of the membrane by incorporating modified carbon products with surface modification that includes metals with the desired catalytic activity.
7. Allow flexibility in the formulation of the membrane composition. Current membranes have most of the chemically selective functionality built into the polymer that is the major component of the membrane. The utilization of modified carbon products in the membrane decouples the functionality of the membrane from the polymer and can enable different combinations of functions that have not been achieved in the past.

None of the known approaches for improving membrane performance can combine the performance enhancements that can be accomplished by incorporating modified carbon products in accordance with the present invention.

The application of modified carbon products can also be extended to membranes for other separations. Generally, membrane separations rely on the ability of the membrane to differentiate the components that need to be separated based on their charge, size, chemical reactivity, solubility, and diffusivity through the membrane. The modified carbon products can enhance the properties of membranes utilized in ultrafiltration, diafiltration, reverse osmosis, microfiltration and other separation processes that require specifically designed membrane materials. The modified carbon products can enhance properties of the membrane that are key to the separation performance and can also enhance other properties, such as the wettability of the membrane by the liquid with which it is in contact and enhance other properties such as permeability.

According to another embodiment of the present invention, modified carbon products can be used in heat transfer applications. Choi et al. (see J. Nanoparticle Research, 5, pp. 167-171 (2003) and references therein) have indicated that conductive nanoparticles dispersed in coolants can provide a significant thermal conductivity increase of the system (>20%), even at very low concentrations. Most of the nanoparticles on which Choi et al. and others have focused include metals (like copper or silver) that have high thermal conductivities but are relatively hard to suspend in a stable dispersion. The stability of the dispersion at a relatively high volume fraction is critical for the effective performance of the composite coolant. In addition, the metallic nanoparticles should not adhere to the heat transfer surfaces. Some of the metallic nanoparticle dispersions (e.g., silver nanoparticles) have a tendency to deposit onto or otherwise coat metallic or glass surfaces, so their utility as a heat transfer enhancing material is reduced.

Choi et al. in U.S. Pat. No. 6,221,275 disclose the enhancement of the thermal conductivity of heat transfer fluids with the addition of nanocrystalline particles. Withers et al. in U.S. Patent Publication No. 2002/0100578 describe the use of carbon nanomaterials to enhance the thermal properties of fluids, focusing on carbon selected from carbon having $sp^2$- and $sp^3$-type bonding. Bonsignore et al. in U.S. Pat. No. 6,432,320 disclose heat transfer compositions including a heat transfer medium and powder additives (metal- or carbon-based and combinations thereof) that are coated with a variety of coatings. Each of these U.S patents and Patent Publications is incorporated herein by reference in its entirety.

Metallic nanoparticles supported on carbon black particles or other thermally conductive supports (e.g., fumed alumina or silica, colloidal alumina or silica, etc.) with a surface that can be surface modified, have been found to have thermal conductivity that is significantly better than that expected from the theory of composites put forth by Maxwell, as is described in Choi et al. (2003). According to the present invention, modified carbon particles can advantageously be dispersible in a variety of coolants by proper surface modification of the carbon support, as compared to the nanoparticles in heat transfer fluids known in the art. For example, particles containing Pt deposited on carbon black can be made dispersible in ethylene glycol/water mixtures by the attachment of a benzenesulfonic group on the carbon surface of the composite particle. As a consequence, these materials can provide enhanced rheological properties in addition to enhanced thermal conductivity. The viscosity of the heat transfer fluid is equally important in its heat transfer performance in convective applications, as is well known in the art. See, for example, Holman, "Heat Transfer", $8^{th}$ edition, McGraw-Hill (1997).

Figure 9:
FIG. 9 illustrates a transmission electron micrograph of platinum dispersed on carbon black surface modified with benzene-sulfonic acid groups according to an embodiment of the present invention.

Some advantages of the supported metal nanoparticle over the unsupported metal nanoparticle suspensions for heat transfer applications can include:

1. The metal particles are fixed on the support and cannot agglomerate. In FIG. 9 a transmission electron microscopy (TEM) photomicrograph of a carbon black aggregate with deposited Pt is illustrated. It is evident from FIG. 9 that the Pt nanoparticles have dimensions significantly smaller than that of the carbon black aggregate and are evenly dispersed on the surface of the carbon black aggregate, so they can not agglomerate.
2. The metal particle formation conditions and the amount of metal on the support can be manipulated to control the size and distribution of the metal particles and to consequently optimize the thermal properties of the dispersion. The Pt nanoparticles shown in FIG. 9 are an example of a 20 wt. % loading of Pt on C. The total loading of metal on the support can be increased or decreased according to the desired performance.
3. The particles will not coat or deposit on the surfaces that are in contact with the dispersion because they will be supported by the surface modified support. This property will enhance the applicability of metallic nanoparticle dispersions by expanding the range of applications.
4. The particles will be more stable because the stabilization of the dispersion will be performed via the surface modification of the support, which is more flexible than that of the metal nanoparticles. The particles shown in FIG. 9 are supported on carbon black, which is subsequently surface modified with benzenesulfonic groups.

These groups in turn help stabilize the dispersion of these particles in water/ethylene glycol mixtures that are typical of heat transfer fluids. In general, stabilized dispersions have better rheological properties (e.g., viscosity, etc.) than unstable dispersions. Stabilized dispersions have a positive impact on the heat transfer fluid's heat transfer properties.

The enhanced performance of these materials can also be extended to other applications, where improved thermal conductivity is important, such as the enhancement of the properties of thermal pastes used as thermal interface materials for the dissipation of heat from microelectronics. Carbon black based dispersions have been reported (Leong et al., Carbon, 41, pp. 2459-2469, (2003)) to have enhanced performance in such applications. The materials that are used in the interface between a heat source and a heat sink should have low contact resistance, should conform to the surface topography of the surfaces that they join and also should have good thermal properties. The materials of the present invention can combine the thermal conductivity of the underlying carbonaceous materials with the enhanced thermal properties associated with the well-dispersed metallic nanoparticles on their surface and the excellent dispersion and compatibility with the matrix that arises from the surface modification of the carbonaceous surface.

Modified carbon products and metal-functionalized modified carbon products also exhibit catalytic activity and can act as catalyst supports in a number of different forms that can range from an anchored metal complex to supported metal nanoparticles that are derived from a metal complex. In the case of metal functionalized carbons that are used as anchored catalytic metal species, the metal species is effectively a homogeneous catalyst that is bound to the carbon surface through the organic functionalization. These supported metal compounds are typically either organometallic, metal-organic complexes or coordination compounds that are typically used on homogeneous catalysts.

The advantages of using carbon as a catalytic support have been explored by many, as reported by the variety of applications for these materials that are listed in Radovic et al. Specifically, carbon-based catalysts have found applications in the area of petroleum refining. Another area of application is that of hydro-desulfurization and/or hydro-denitrogenation where state-of-the-art catalysts include Mo, Co, Co—Mo or Ni—Mo supported on γ-alumina. There are reports that replacing or coating the alumina with carbon can lead to enhanced catalyst performance. Many applications are also described in Radovic et al. and its references. For example, hydrogenation reactions where Pd/C. (i.e., palladium on carbon), Pt/C, Fe/C, Ni/C, Ru/C, Pt—Ru/C, and various alkali metal promoted combinations of metals supported on carbon can be used for reactions as diverse as the reduction of nitroaromatics to ammonia production. In oxidation reactions, especially liquid phase oxidations of alcohols to aldehydes, ketones, or carboxylic acids, catalytic transition metals, such as Pt, Pd, Ru, Ir, and others alone, in mixtures/alloys, or enhanced by addition of selected elements (e.g. bismuth) supported on carbon have demonstrated increased activity and selectivity. There are a wide variety of other applications, including environmental applications, for the removal/reduction of $SO_x$, $NO_x$ and other acid gas pollutants.

The modified carbon products of the present invention are an ideal medium for supporting catalysts because they have enhanced properties compared to the catalysts prepared using established methods. The performance of catalysts that are supported depends on a variety of properties of the support.

The physical properties of the support determine how usable it is in the application. The particles should have a specific size so that they can be easily handled and utilized in the process. They need to be rigid so that they don't disintegrate during use leading to the creation of fines and the loss of the catalyst. Their pore structure should be suitable for the diffusion of the reagents and products to and from the active catalytic sites.

The surface properties of the support play an important role in determining the activity of the catalyst because they influence the dispersion of catalyst on the surface of the support. The surface chemistry is also influential and can enhance or interfere the transport of reagents and products to and from the catalyst particles.

The materials of the present invention allow the design of the catalyst properties at all levels. Specifically, these carbonaceous materials feature carefully controlled particle size and particle size distribution, microstructure and pore size distribution, rigidity, and flexible surface chemistry that can be tailored for any specific application.

The materials of the present invention are unique because they can range in size from less than 100 nm (the size of a carbon black aggregate or a single-walled carbon nanotube) to several or hundreds of microns (the diameter of a carbon fiber or the size of a spray processed carbonized resin-bound carbon black particle). The larger particles can have tailored porosity that can be determined by:

1. the morphology of the constituent carbon blacks.
2. the concentration and type of binder used to bind the carbon black aggregates
3. the conditions for curing and/or carbonizing the binder; and
4. the incorporation of reverse templating materials with desired morphologies that can be removed from the particles after the particle formation by dissolution, acid or base treatment, or other techniques known in the art.

The materials of the present invention can also have tailored surface chemistry that allows control over the design of the catalyst particle at the molecular level. This ability can enhance several aspects of the catalyst from its manufacturing processes to its final performance. For example, tailoring the surface before the deposition of the catalyst metal by attaching functional groups that have high affinity for the metal can enable a more uniform distribution of the metal particles. Modifying the surface with groups (e.g., ionic groups or hydrophilic polymer groups) that enable the starting carbon black particles to fully disperse in the precursor solution can enhance the uniformity of deposition of metal particles because the entire surface of the particle will be wetted and accessible. The modification of the surface with custom groups can also occur after the metal deposition depending on the intended application. This may facilitate processes such as the application of catalytic coatings on membranes, monoliths or other devices that may benefit from the presence of a carbon-supported catalyst.

The current art focuses almost exclusively on oxygenated groups that are either present on the carbon surface or can be incorporated by a variety of oxidation techniques as the only way to influence the carbon surface chemistry (see for example Radovic et al., in "Chemistry and Physics of Carbon: A Series of Advances, Vol. 25", Marcel Dekker, (1997), pp. 243-358, and all references within). The present invention expands the range of functionalities that are possible on the carbon surfaces to a broad spectrum of organic and inorganic groups. The ability to surface modify carbon coated on inorganic oxides, enables the combination of unique surface chemistries of materials such as alumina or silica with the enhanced metal dispersion on the carbon fraction of the surface.

A few of the several new capabilities of the materials of the present invention are described below.

1. Metal-containing catalysts supported on carbon black aggregates that are surface modified to become dispersible in the reaction medium, thus enabling better contact and transport and yielding higher activity. Because of the submicron size of the particles this system is expected to behave as a quasi-homogenous system, showing enhanced performance.

2. The surface modification enables the preparation of totally new catalytic materials. Trends in catalysis are moving towards immobilized homogeneous catalysts that are easily removable from the reaction matrix and help improve productivity by reducing costs associated with product purification and precious metal loss and recovery (see for example S. Buckley, "Innovations in Catalysis" in Manufacturing Chemist, Jan. 19, 2002). The carbonaceous materials of the present invention can be surface modified with groups that either contain or can be reacted further to incorporate homogenous catalysts. Examples of such catalysts include: a) carbon supported Pd—P(Ph)$_3$ containing catalysts used in Suzuki or Heck reactions in organic synthesis, b) carbon supported Rh—P(Ph)$_3$ containing catalysts used in hydrogenation reactions, c) carbon supported Pt-complex containing hydrosilation catalysts. Virtually any organometallic complex that can act as a homogeneous catalyst can be supported on a carbonaceous support using the methods of this invention. The improved carbon supported homogeneous catalysts are expected to match the performance of the original homogeneous catalysts. Other supported homogeneous catalysts that are known in the art utilize polymer supports to anchor the homogeneous catalyst. The homogeneous catalyst is covalently bonded to inert polymer fibers that then swell to allow for diffusion of reagents to and from the active sites. This is why these materials are known to have comparable activity to homogenous catalysts, but suffer in that the reaction times are longer. The rigidity of the carbon support and the flexibility in terms of the morphology of the carbonaceous particles provide distinct advantages. The ability to create homogeneous supported catalysts on sub-micron carbon black aggregates combined with dispersion allow for ease of contact of the reagents with the active sites.

According to another embodiment of the present invention, the homogeneous catalysts are strongly bonded to the surface of the modified carbon products (including particle and fiber-based materials), and therefore the separation of the catalytic species from the reaction medium can be very efficiently achieved. This separation is a problem in many cases in which the products of the reaction may be contaminated by the presence of residual catalytic species, which also leads to loss of often expensive precious metal based catalytic reagents.

Another embodiment of the present invention is directed to the use of modified carbon products including metal-functionalized modified carbon products in chemical separation applications. Here, what is desired is a surface moiety that binds a molecule (metal or non-metal containing) and elutes it under a different set of conditions, such as increased or decreased pH, i.e., pseudo-reversible. This overall process is useful in a number of applications ranging from chromatography to immunoassays (as described by Kang et. al in U.S. Pat. Nos. 6,506,612, 5,559,041 and 5,529,901 which are incorporated herein by reference in their entirety) where a series of molecules are traditionally being separated form one another, to quantitative separation (of, for example, one molecule or ion from another including the recovery of the material that is separated and the quantitative recovery of the material from which it is being separated) to sensing applications where typically a single molecular species is selectively bound. Here, there are a wide variety of sensing applications ranging from more mundane proton sensing to the sensing of bio-hazardous materials.

In some cases, it is advantageous to selectively bind, but not remove, a chemical species. In this case, the modified carbon products act as an adsorbent and also as a scrubbing material. An example of this is the selective removal of mercury (Hg) from waste streams by sulfur functionized moieties like thiols (mercaptans) which are excellent σ donors and hence have an affinity for transition metals. In many cases, mercury is present in gas streams at low concentrations (e.g., <100 ppm by weight) allowing the removal of mercury by running the gas through a bed containing a high surface area modified carbon product with a high concentration of thiols on the surface, preferably a concentration of more than 2 $\mu mol/m^2$, more preferably more than 4 $\mu mol/m^2$.

This embodiment of the present invention can be extended to a wide range of metals and gases that are potentially environmentally dangerous or toxic, even if in low concentration. Other examples of species which can be selectively, irreversibly removed include $H_2S$, HCN, $NO_x$, $SO_x$, as well as other heavy metals such as cadmium, lead and the like.

According to another embodiment of the present invention, a fuel containing an organic sulfur derivative may be partially converted into another chemical form (such as reforming to partially convert to $H_2$) and in the process, the organic sulfur species is converted to $H_2S$. The $H_2S$ is removed in a subsequent step by adsorption onto the surface of suitably functionalized modified carbons prior to another step (e.g., a shift reaction) which would otherwise be poisoned by the presence of $H_2S$.

In another embodiment of the present invention, certain organic molecules can be removed from fluids of gases using suitably modified carbon materials. Examples include removal of thiophene and other sulfur-based organics by coordination to thiophilic MCB-anchored metal species such as Mo or Fe species. These organics can be removed from liquids such as high sulfur content fuels including diesel and JP-8 (military fuel) and other fuels such as natural gas. These fuels typically have a high organic sulfur content (e.g. 500 ppm) and need to be removed prior to further processing of the fuel, which will otherwise result in the formation of $H_2S$. The $H_2S$ thus formed would be poisonous to subsequent chemical processing steps if the fuel is to be reformed into hydrogen, or in the environment if the fuel is used for other purposes (such as combustion).

According to another embodiment of the present invention, it is possible to derivatize the surface of a carbon product to differentially adsorb one molecule in the presence of another through shape specific adsorption onto a modified carbon product surface. An example is the adsorption of a sterically hindered sulfur compound or amine versus and non-sterically hindered one. An example of a sterically hindered sulfur compound is 2 methyl (or i-propyl or tert-butyl)thiophene compared to the non-hindered derivative of thiophene or 3-(or 4-) methyl (or 1-propyl or tert butyl)thiophene. In general, it is possible to distinguish organic molecules with similar functionalities but different steric requirements. This is achieved through the bonding of a metal center to the surface of a modified carbon product with a metal in a ligand environment comprising a sterically crowded coordination sphere and a certain number of labile ligands (preferably one). In a case where two molecules are to be separated, the less sterically hindered species is bound to the metal site more strongly compared to more sterically demanding species (or the more sterically hindered species may not be bonded at all). The order of selective binding of sterically demanding ligands (e.g., $PH_3$ bound to a nickel center versus $P(Ph)_3$ bound to a nickel center) may be predicted based on the concept of Tolman's Cone Angle (Tolman, C. A. Chem. Rev. 77, 313, 1977).

According to another embodiment of the present invention, modified carbons can be derivatized to increase their hydrogen storage capacity and further tailored to affect the temperature and equilibrium of the hydrogen adsorption/desorption kinetics.

Certain absorbent materials can reversibly store hydrogen ($H_2$). Hydrogen storage materials are normally categorized into three different classes according to their compositions and whether the mechanism for hydrogen storage is based on chemisorption or physisorption. Each class of materials has unique properties in terms of the conditions (temperature, pressure, capacity, reversibility) of hydrogen adsorption and desorption, which in turn determine the operating range and possible applications.

One type of hydrogen storage material is a metal alloy or intermetallic compound that includes a mixed metal, often referred to as a mixed metal hydride. Typical mixed metal compositions include AB, $AB_2$, $AB_3$, $AB_5$ and $A_2B$, where A can be selected from lanthanide elements (e.g., La, Ce, Pr, Nd, Pm, Sm, Eu, Gd, Tb, Dy, Ho, Er, Th, Yb and Lu) as well as Mg, Ti and Zr, and B can be selected from the transition elements (e.g., Sc, Ti, V, Cr, Mn, Fe, Co, Ni, Cu, Zn, Y, Zr, Nb, Mo, Rh, Ru, Pd, Ag, Cd, La, Ce and the like). See Zuttel, Materials Today, September 2003, pp. 24-33 which is incorporated herein by reference. Preferred examples of such materials include $LaNi_5$, $Mg_2Ni$, $Mg_2Fe$, TiFe, and $ZrMn_2$ (Argonne National Laboratories Report "Basic Research needs for the Hydrogen Economy", 2003). For example $LaNi_5$ forms a species with the empirical formula $LaNi_5H_{6.5}$ and is the material of choice for nickel/metal-hydride batteries. Other examples are given in G. Sandrock, Journal of Alloys and Compounds, 293-295 (1999) 877-888, which is incorporated herein by reference. These materials currently have the most reliable reversible hydrogen uptake and are currently in use in nickel-metal hydride batteries. They are also the material most commonly used for hydrogen storage, but are not optimal because their gravimetric hydrogen uptake capacity is relatively low, between 1 and 3 wt. %. In addition, these materials typically decrepitate after the first adsorption/desorption cycle to form a powder that is pyrophoric when exposed to air.

Another class of hydrogen storage material is referred to as chemical hydrides. Chemical hydrides are stoichiometric chemical compounds, typically molecular or oligomeric, but which can stoichiometrically reversibly chemically react with, or release, hydrogen. In order to have a relatively high gravimetric hydrogen storage capacity, these materials usually include the hydrides of the lighter elements such as Mg, B, Al, Li, Na, or complexes thereof, including $NaBH_4$, $AlH_3$, $LiAlH_4$, $Mg(AlH_4)_2$. These materials can have hydrogen storage capacities of up to 9 wt. %. For example, $NaAlH_4$ reversibly reacts to form ⅓ $NaAlH_6$+⅔ $Al+H_2$ which can further reversibly react to form $NaH+Al+½ H_2$. The theoretical hydrogen storage capacity for this reaction is about 5.6 wt. %.

Another promising material is LiBH$_4$, which has the highest gravimetric hydrogen density currently known (≈18 wt. %), as described by Zuttel.

In this same class of chemical hydrides, although at the interface of the categorization with the metal alloys and intermetallic compounds, are some specific metal hydride compositions which form a known alloy phase on loss of hydrogen. An example of such as compound is Mg$_2$NiH$_4$ which forms 2H$_2$ and Mg$_2$Ni alloy. Another example is Mg$_2$FeH$_6$, which has the potential for 5.5 wt. % hydrogen storage.

In general it is believed that the addition of dopants or catalysts can enhance the storage capacity, kinetics, and regenerability of most chemical hydrides. For example, in the case of complex metal hydrides, the addition of a Ti Catalyst to sodium alanate (NaAlH$_4$) described by Bogdanovic and Sandrock (MRS Bulletin, September 2002, pp. 712-716) led to a reversible capacity of >4 wt. % at 150° C., conditions not too far from ambient. In the case of simple metal hydrides, Barkhordian et al. (Scripta Materialia, 49, (2003), pp. 213-217) have shown that the incorporation of Nb$_2$O$_5$ and other metal oxides into Mg can have a significant effect on the adsorption and desorption kinetics of MgH$_2$.

Other materials that chemically store hydrogen have been reported, such as alkali metal nitrides and imides and especially lithium-based compounds such as Li$_3$N, reported by Chen et al. (Nature, 420, (2002), pp. 302-303) that were shown to reversibly adsorb and desorb hydrogen with storage capacities higher than 5 wt. %.

The third class of hydrogen storage materials are those that physisorb hydrogen, which are typically highly microporous nanostructured materials. A range of such materials is described by Nijkamp et al. (Applied Physics A, 72, (2001), pp. 619-623) which is incorporated herein by reference. These materials are usually inorganic carbon or silica or alumina based materials with high pore volumes, such as activated carbons, zeolites and others. However, there have been reported examples of organic/metalorganic materials with tailored nanostructures, such as those reported by Rosi et al. (Science, 300, (2003), pp. 1127-1129).

The most promising of these materials include carbon particles, carbon nanotubes or fullerenes and may also have present other hetero atoms which enhance the hydrogen uptake. These carbon-based materials can also have surface funtionalization groups that enhance the capacities and kinetics of hydrogen storage. High surface area active carbons have long been known to physisorb molecular hydrogen, but only at low temperatures due to the weak nature of the physisorption interaction. At the other extreme, chemical reaction of hydrogen with carbon (chemisorption) in the form of fullerenes to form hydrocarbons, e.g., C$_{60}$H$_{48}$, results in the formation of covalently bonded hydrogen that requires too high a temperature for desorption of the hydrogen. To resolve this dichotomy, a number of solutions have been explored. A reduction in the chemical stability of the "carbon hydrides" can be conceived to bring the adsorption/desorption kinetics closer to room temperature. Single wall carbon nanotubes have dimensions that are close to that required for capillary condensation of hydrogen molecules and may offer an alternative strategy. Finally, the incorporation of metal particles into the structure of the carbon particles could provide another mechanism to bring the reaction conditions closer to more commercially relevant conditions. A recent example was described in U.S. Patent Application Publication No. 2002/0096048 by Cooper et al., which is incorporated herein by reference in its entirety.

The reversible hydrogen storage material includes metals, such as Pt, or metal alloys, mixed with or dispersed on the surface of the carbon particles. The carbon particles may also be modified on their surface with organic functional groups to enhance their absorption capability in a number of different ways. One mechanism in which surface modification plays a role is in the ability to selectively bind a catalytically active material such as a molecular metal-containing complex or a nanometer-sized catalytically active particle such as a metal. Modified carbon blacks comprising metal particles are described in U.S. Pat. Nos. 6,399,202, 6,280,871, 6,630,268, 6,522,522, U.S. Patent Application Publication No. 2003/0017379 and U.S. Patent Application Publication No. 2003/0022055, each of which is incorporated herein by reference in its entirety. The surface functional groups also affect the uptake of the gaseous species that is being absorbed, such as hydrogen, by changing the packing characteristics of the carbon particles as well as the carbon surface characteristics to be, for example, hydrophobic or hydrophilic. Typical surface function groups include carboxylic acids, sulfonyllic acids, amines and the like. A method by which the surface of the carbon particles can be modified is through reactions with diazonium salts of the desired organic functional groups, as described by Belmont et al. in U.S. Pat. Nos. 5,851,280, 6,494.946, 6,042,643, 5,900,029, 5,554,739 and 5,672,198, which are incorporated herein by reference in their entirety.

There are also other types of materials that exhibit hydrogen storage properties. These include a number of carboxylate compounds such as zinc acetate and others.

There are several aspects to the design of hydrogen storage materials which must be successfully addressed in order for them to have value in practical commercial applications. Some have been outlined by Sandrock et al. (Journal of Alloys and Compounds, 330-332, (2002), pp. 696-701). They must have a reasonable reversible hydrogen storage capacity. The US DOE targets for automotive applications are currently 6.5 wt. % hydrogen. Hydrogen storage materials must also exhibit a reproducible capacity over many cycles of hydrogen uptake under conditions of temperature and pressure, which are preferably close to room temperature and pressure. The materials must also have good low-temperature kinetics and equilibrium plateau pressures. They must perform well and be reversible under the highly exothermic charging steps and must be incorporated in systems with good thermal management. In addition, like most sorbents, materials that chemically store hydrogen expand during the adsorption step, and become embrittled. Ideally, the materials should remain intact during the course of the reversible hydrogen uptake and avoid decrepitation which can have serious operational and safety issues.

It is well known that carbon materials including graphites, carbon blacks and nanotubes reversibly adsorb H$_2$. Furthermore, it has been demonstrated that capacity and reversibility of H$_2$ adsorption by carbon can be improved by dispersing various other materials such as metals over the carbon surface. The value of surface modification of carbons to improve the performance of hydrogen storage materials can be manifested in a number of different ways. The surface can be modified with functional groups, which bind hydrogen-rich molecules that are known to reversibly and stoichiometrically liberate and react with hydrogen. Examples of compounds in this class are the donor adducts (e.g. amine adducts) of boranes and alanes of salts thereof including but not limited H$_3$BNH$_3$, LiBH$_4$, (CH$_3$)$_4$NBH$_4$, Al(BH$_4$)$_3$, Mg(BH$_4$)$_2$ LiH, AlH$_3$, MgH$_2$, NaAlH$_4$, Mg$_2$FeH$_6$, BaReH$_9$, LaNi$_5$H$_6$ and Mg$_2$NiH$_4$. In another embodiment of this invention, the surface functional groups may be comprised of metal-containing molecules that are well known to reversibly undergo redox chemistry to form metal hydride complexes. There are a variety of metal di-hydrogen complex is in this class (including $L_2PtH_2$, $(L_2)_2Fe(H_2)_2$, $IrL_2H(H_2)_2$, where L is a electron pair donating ligand. The presence of these species on the surface of the carbon material may serve to adjust the temperature and pressure of reversible adsorption of hydrogen into the carbon-based material.

In a further embodiment of this invention, the surface modification can be used to bind metal species like group IA, IIA and IIIA metals and mixtures thereof to the surface of the carbon particles which act as precursors (as described above) for the formation of highly dispersed (nm-sized) metals or metal-based species (such as nitrides, carbides). The resulting materials can form reversible hydrogen storage materials, like complex hydrides. The highly dispersed metals can also form intermetallic compounds with structures like AB, $AB_2$, $AB_5$ and $AB_3$ like TiFe, $ZrV_2$, $LiNi_5$ and $CaNi_5$. In this embodiment the highly dispersed phase may act as a catalyst to split hydrogen molecules for adsorption onto the surface of the carbon and/or may serve to increase the total hydrogen adsorption capacity of the material. Since the best hydrogen storage materials typically only have a reversible $H_2$ storage capacity of less than 2 wt. % hydrogen, a small improvement can have an enormous impact. These materials can be used to store hydrogen for fuel cell applications and for metal hydride-based battery applications, as well as provide an alternative technology for the storage and transportation of hydrogen as a chemical. US patent application, 2002 009 604 8 A1, Cooper et al. is incorporated herein by reference in its entirety.

Modified carbon products for use in adsorbent applications are disclosed in WO 09747382A1, and U.S. Patent Application Publication Nos. 2004/028901, 2002/117446, 2003/042205 and 2002/0056686, the disclosure of each of which is incorporated herein by reference in its entirety.

Modified carbon products may also be used as adsorbents or "getters" for volatile species present in electronic devices such as displays. In this application, a high surface area material that irreversible binds volatile species that may be present is desired to avoid a reduction in device performance caused by the reaction of the volatile species with an active component in the display. Furthermore, because the modified carbon products, such as modified carbon black is also a black pigment that can be used to construct the black matrix in a flat panel display, the modified carbon material may now exhibit a dual functionality of the black matrix and a getter for unwanted materials.

In a further embodiment of this invention, the modified carbon materials may also be used to desorb species that are coordinated to the modified carbon surface. This may take the form of a slow release over time or could be induced through, pressure, pH mechanical activation or temperature changes. In a typical example, coordinated molecule with particular fragrance characteristics could be released from an article such as a watch strap or an article of clothing that is comprised a modified carbon product (such as a fiber or cloth).

In a further embodiment of this invention, antimicrobial and/or antibacterial species may be bonded to the surface of the modified carbon product. An example of such a functionalized material is a dispersion of silver nanoparticles on the surface of a modified carbon product. It is well known that silver imparts antibacterial activity both in the form of silver metal and silver complexes. The dispersion of the silver species over the surface of a high surface area functionalized carbon is an effective way to deliver the anti bacterial activity to the point of use. An example of an application of this material is in a cream or spray that can be applied to a wound or as part of a surgical wrap or plaster, that is applied to a skin opening to prevent infection.

According to the present invention, modified carbon materials may be surface functionalized with organic groups that serve as ligands that bind light-emitting materials and such an approach has been demonstrated in the past for luminescent assays on carbon nanotubes (see Massey et. al, U.S. Pat. No. 5,866,434, which is incorporated herein by reference in its entirety). In particular, these materials may be chosen from the group of molecular species that are known to luminesce such as rare-earth molecules like Eu, Tb, Er, etc. and also light emitting organics and polymers typically used in organic light emitting diode applications including but not limited to tris-8-hydroxyquinoline aluminum ($Alq_3$), N,N'-diphenyl-N,N'-(3-methylphenyl)-1,1'-biphenyl-4,4'-diamine (TPD), and poly(para-phenylenevinylene) (PPV).

In one preferred embodiment of this aspect of the invention, highly anisotropic carbon particles such as nanotubes or carbon fibers are derivatized with molecular electroluminescent molecules that are encapsulated into an insulating matrix. When the matrix comprising these modified carbon materials is placed in an electric field, electroluminescence occurs at the high fields generated at the tips of the anisotropic carbon particles. This phenomenon is analogous to the mechanism of powder electroluminescence that has been described in Shionoya, S., Yen, W. Eds. *The Handbook of Phosphors*, CRC Press, 1998. The dielectric matrix may be either inorganic based (e.g. a dielectric metal oxide; an organic polymer of a combination of the two.

The present invention is also applicable to infrared (IR) emitting phosphors. The luminescence centers can be attached to the modified carbon products, wherein the luminescence centers absorb radiation at a wavelength above the infrared, but emit light in the IR region. Such products are useful, for example, in military applications where IR emitting phosphors can be used to discern friendly troops or equipment.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. A modified carbon product comprising a carbon support having a carbon surface, and an organic group having a cyclic portion and a functional group attached to the carbon surface and a metal group covalently attached to said functional group, wherein said metal group is a metal source that is silver, copper, nickel, europium, iron, aluminum, rhodium, cobalt, ruthenium, magnesium, calcium, or platinum.

2. A modified carbon product as recited in claim 1, wherein said metal group is ionically attached to said functional group.

3. A modified carbon product as recited in claim 1, wherein said modified carbon product is operably useful in electrodialysis.

4. An electrical conductor comprising the modified carbon product as recited in claim 1.

5. An ionic conductor comprising the modified carbon product as recited in claim 1.

6. A method to conduct an immunoassay utilizing the modified carbon product as recited in claim 1.

7. A method to conduct electroluminescence utilizing the modified carbon product as recited in claim 1.

8. A method to conduct luminescence utilizing the modified carbon product as recited in claim 1.

9. A thermally conductive fluid comprising the modified carbon product as recited in claim 1.

10. A method to conduct hydrogen storage utilizing the modified carbon product as recited in claim 1.

11. A method to conduct catalysis utilizing the modified carbon product as recited in claim 1.

12. A capacitor comprising the modified carbon product as recited in claim 1.

13. A sensor comprising the modified carbon product as recited in claim 1.

14. The modified carbon product as recited in claim 1, wherein said carbon support is activated carbon, bulk carbon, carbon flakes, carbon fibers, or carbon nanotubes.

15. The modified carbon product as recited in claim 1, wherein said carbon support comprises carbon black.

16. The modified carbon product as recited in claim 1, wherein said carbon support comprises a carbon nanotube.

17. A method for the manufacture of a modified carbon product, comprising the steps of:
   a) providing a carbon support;
   b) modifying said carbon support by reacting a diazonium salt in the presence of said carbon support to provide an organic group that attaches to a carbon surface of said carbon support, wherein said organic group has a cyclic portion and a functional group, wherein said modifying step comprises the step of spray processing a precursor solution comprising said carbon support; and
   c) attaching a metal group to said functional group, wherein said metal group is a metal source that is silver, copper, nickel, europium, iron, aluminum, rhodium, cobalt, ruthenium, magnesium, calcium, or platinum, wherein said metal group is covalently attached to said functional group.

18. A method as recited in claim 17, wherein said carbon support comprises carbon black.

19. A method as recited in claim 17, wherein said functional group is ionically charged and coordinating.

20. The method as recited in claim 17, wherein said modifying said carbon support comprises reacting the carbon support with a diazonium salt functionalizing agent comprising the structure:

where X reacts with a carbon surface of the carbon support; $R^1$ is $C_6H_4$ and $C_{10}H_6$; and Y is said functional group.

21. The method as recited in claim 20, wherein said functional group is —SO$_3$H, —CO$_2$H, —PO$_3$H$_2$, —PO$_3$NaH, —CF$_3$, —CONR$_2$, —NR$_3^+$, —NR$_2$, —PR$_2$, where R is alkyl, aryl, hydrogen, or any combination thereof.

22. The method as recited in claim 17, wherein the carbon support is combined with at least one diazonium salt and a metal containing species, and the resulting combination is spray-processed to modify the carbon support with the functional group and attach the metal group to the functional group.

23. The method as recited in claim 17, wherein a metal containing species is combined with the functional group modified carbon support, and the resulting combination is spray-processed to attach the metal group to the functional group.

24. The method as recited in claim 17, wherein the attaching step comprises reacting a dissolved or suspended metal-containing reagent metal with the functional group modified carbon support in a liquid medium.

25. The method as recited in claim 17, wherein the attaching step comprises reacting a vapor phase metal-containing reagent with the carbon support with a functional group.

26. The method as recited in claim 17, wherein the attaching step comprises fluidizing the carbon support with the functional group and reacting a gaseous metal-containing reagent with the carbon support with the functional group.

27. The method as recited in claim 17, wherein the carbon support is carbon black, activated carbon, bulk carbon, carbon flakes, carbon fibers, or carbon nanotubes.

28. The method as recited in claim 17, wherein the carbon support comprises a carbon nanotube.

29. The method of claim 17, wherein the step of spray processing said precursor solution comprising said carbon support comprises providing a liquid precursor suspension including the carbon support as carbon particles and the diazonium salt or a precursor to the diazonium salt; atomizing the liquid precursor suspension to form dispersed liquid precursor droplets; removing liquid from the dispersed liquid precursor droplets and converting the diazonium salt to said organic group attached the carbon surface, to form a modified carbon support.

30. The method of claim 29, further comprising adding a metal containing species that is silver, copper, nickel, europium, iron, aluminum, rhodium, cobalt, ruthenium, magnesium, calcium, or platinum, to the liquid precursor suspension prior to said atomizing.

* * * * *